United States Patent
Cummings et al.

(10) Patent No.: US 7,241,265 B2
(45) Date of Patent: Jul. 10, 2007

(54) ANALYTE TESTING DEVICE

(75) Inventors: Elizabeth A. Cummings, San Jose, CA (US); Mary E. McEvoy, Belmont, CA (US); Lars H. Berger, Deuerling (DE); Ulrich Kraft, Oberursel (DE); Rainer R. Teucher, Friesheim (DE); John C. Davis, Los Altos, CA (US)

(73) Assignee: Diabetes Diagnostics, Inc., Waltham, MA (US)

( * ) Notice: Subject to any disclaimer, the term of this patent is extended or adjusted under 35 U.S.C. 154(b) by 0 days.

(21) Appl. No.: 10/454,559

(22) Filed: Jun. 3, 2003

(65) Prior Publication Data

US 2004/0015102 A1 Jan. 22, 2004

(30) Foreign Application Priority Data

Jun. 5, 2002 (GB) ............................................. 0212920

(51) Int. Cl.
*A61B 5/00* (2006.01)

(52) U.S. Cl. ........................ 600/300; 128/920; 600/347; 600/365

(58) Field of Classification Search ......... 600/300–301, 600/347, 361, 365, 316, 309, 368; 434/236–238, 434/262, 267; 128/897, 898, 920–921, 903, 128/904; 705/2–4; 604/207; 340/573.1; 482/8–9, 482/90; 235/375, 385
See application file for complete search history.

(56) References Cited

U.S. PATENT DOCUMENTS

| | | | |
|---|---|---|---|
| 4,731,726 A | | 3/1988 | Allen, III |
| 5,307,263 A | * | 4/1994 | Brown ........................ 600/301 |

(Continued)

FOREIGN PATENT DOCUMENTS

| | | |
|---|---|---|
| EP | 0290683 A2 | 11/1988 |
| EP | 0415679 A | 3/1991 |
| EP | 0475692 A | 3/1992 |
| EP | 0656423 A | 6/1995 |
| EP | 0735369 A | 10/1996 |
| GB | 2218831 A | 11/1989 |
| WO | 00/32258 A1 | 6/2000 |
| WO | WO 01/89368 A2 | 11/2001 |
| WO | 02/015702 A2 | 1/2002 |

OTHER PUBLICATIONS

Abstract of Japanese Patent No. 2000139844, Kuroyanagi, Nov. 6, 1998 "Portable Self–Control Device".
Abstract of Japanese Patent No. 11056822, Omron Tateisi Electronics Co., Aug. 19, 1997 Blood Sugar Measuring Instrument.
United Kingdom Search Report, The Patent Office, Newport, South Wales, UK, Mar. 17, 2005, for UK Patent Application 0212920.3.
European Search Report, The European Patent Office, The Hague, Netherlands, Mar. 3, 2005, for European Patent Application 02078709.9.

(Continued)

*Primary Examiner*—Max F. Hindenburg
*Assistant Examiner*—Michael Astorino
(74) *Attorney, Agent, or Firm*—Bernard E. Shay

(57) ABSTRACT

The present invention is a testing device for testing analyte levels in bodily fluids. The testing device comprises memory (202) for storing data, said data being analyte data related to analyte measurements carried out by the meter and lifestyle data; initiation means (102) for initiating immediate entry of data related to a specific category of lifestyle data; navigation means (104) for entry and navigation of said data; and transfer means (258) for transferring said data to said memory. Preferably, the testing device is a glucose meter and one of the analytes being tested is glucose.

17 Claims, 18 Drawing Sheets

U.S. PATENT DOCUMENTS 5,507,288 A * 4/1996 Bocker et al. .............. 600/322
5,822,715 A * 10/1998 Worthington et al. ......... 702/19
5,840,020 A 11/1998 Heinonen et al.
6,024,699 A * 2/2000 Surwit et al. ................ 600/300
6,656,114 B1 * 12/2003 Poulsen et al. ............. 600/300

OTHER PUBLICATIONS

First Office Action from Patent Office of the People's Republic of China, Bejing, China dated Jul. 29, 2005 in reference to Chinese Patent Application 03141002.2.

Chinese Publication No. CN1337209A Non–Injurious Household Cardiovascular Function Detecting Method, Feb. 27, 2002.

Chinese Publication No. CN1074365A Tumor Image Diagnostic Method and System, Jul. 21, 1993.

Owner's Booklet "One Touch Profile Diabetes Tracking System", LifeScan, Inc., Milpitas, California, U.S.A. pp. 320–422 Jun. 1995.

LifeScan: New Meter/Electronic Logbook Combo Helps People with Diabetes Spot Patterns in Blood Glucose levels [Online] Mar. 18, 2003 XP002394706 Milpitas, California, Retrieved from the Internet: URL: http://wwww/lifescan.com/company/about/press/prultrasmart [retrieved on Aug. 14, 2006], 2 pgs.

* cited by examiner

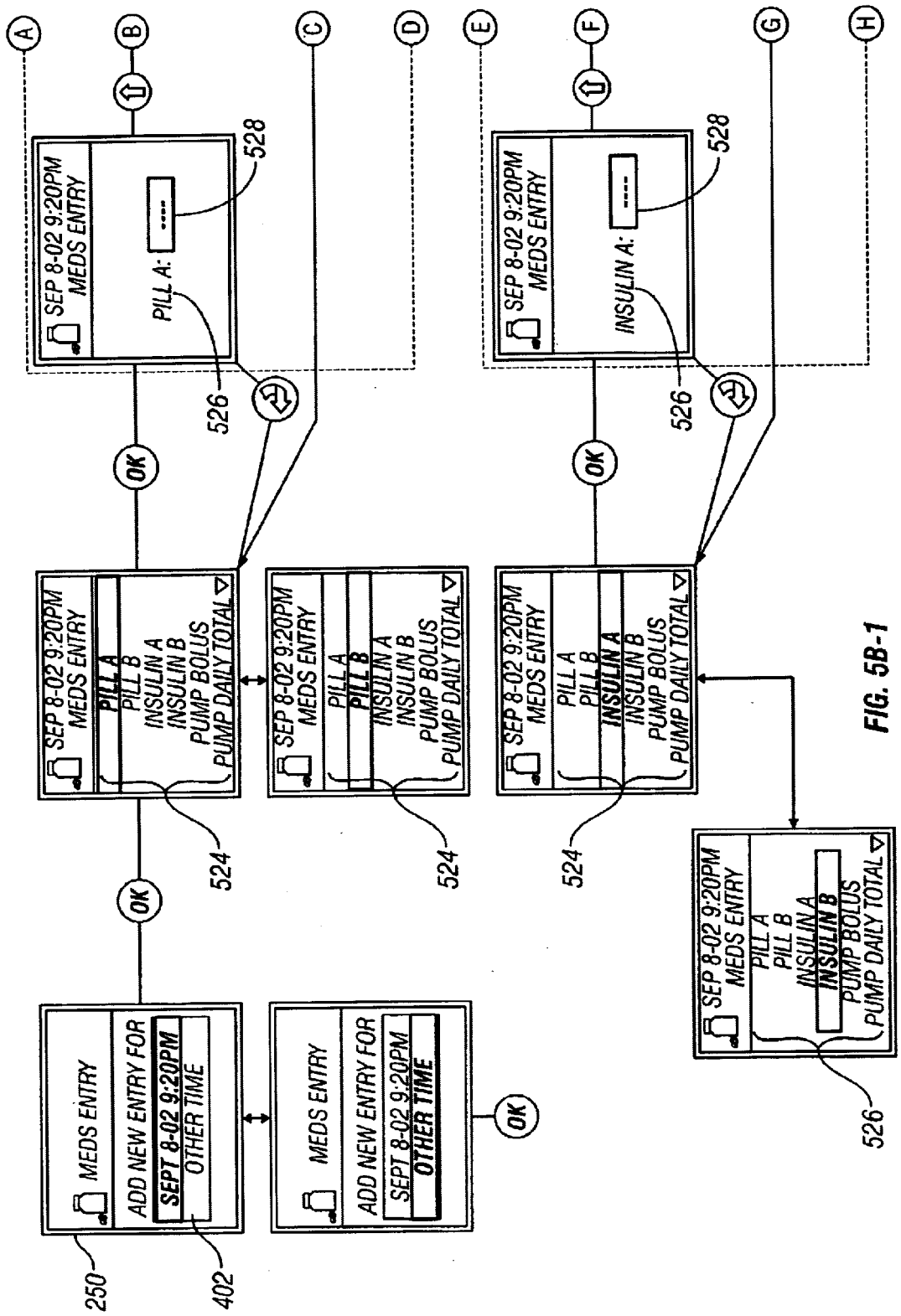

ANALYTE TESTING DEVICE

CROSS REFERENCE

This application claims priority to UK Application No. 0212920.3, filed Jun. 5, 2002, which application is fully incorporated herein by reference.

FIELD OF THE INVENTION

The present invention relates to a testing device for testing analytes in samples of bodily fluid and storing and analysing lifestyle data, which may not be analyte related. A preferred use of the testing device is for testing the glucose level in the blood of individuals, including people with diabetes. Lifestyle data may, for example, comprise data related to the food consumption, exercise level, medication intake or other health related data of an individual. An example of a use for such a testing device is by physicians, who routinely need to make an assessment of an individual's lifestyle.

BACKGROUND OF THE INVENTION

Glucose monitoring is a fact of everyday life for diabetic individuals. The accuracy of such monitoring can significantly affect the health and ultimately the quality of life of the person with diabetes. Generally, a diabetic patient measures blood glucose levels several times a day to monitor and control blood sugar levels. Failure to test blood glucose levels accurately and on a regular basis can result in serious diabetes-related complications, including cardiovascular disease, kidney disease, nerve damage and blindness. There are a number of electronic devices currently available which enable an individual to test the glucose level in a small sample of blood. One such glucose meter is the OneTouch® Profile™ glucose meter, a product which is manufactured by Lifescan.

In addition to glucose monitoring, diabetic individuals often have to maintain tight control over their lifestyle, so that they are not adversely affected by, for example, irregular food consumption or exercise. In addition, a physician dealing with a particular diabetic individual requires detailed information on the lifestyle of the individual to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distil or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

Moreover, a diabetic individual often has to keep a plurality of devices on their person for diagnosis and treatment, for example both glucose level monitoring equipment and medication. Hence, having to carry paper records of their lifestyle is an added unwanted burden and entry of data therein is very time consuming.

There currently exist a number of portable electronic devices that can measure glucose levels in an individual and store the levels for recalling or uploading to another computer for analysis. On such device is the Accu-Check™ Complete™ System from Roche Diagnostics, which provides limited functionality for storing lifestyle data. However, the Accu-Check™ Complete™ System only permits a limited selection of lifestyle variables to be stored in a meter. Also, there are only three navigation buttons on the meter, which makes it difficult to input lifestyle data. There is a no intelligent feedback from values previously entered into the meter and the user interface is unintuitive for an infrequent user of the meter.

Therefore, what is required is an electronic device for logging and analysing lifestyle data, which does not increase the number of devices an individual has to keep on their person and is also more intuitive and easier to use than other devices, thereby encouraging an individual to record information related to their lifestyle. Lifestyle data should be taken to mean any quantifiable information which might affect or represent an individual's physical condition. Examples of lifestyle data are food consumption, physical exertion (e.g. exercise), medication intake and health checks performed on the individual.

SUMMARY OF THE INVENTION

In view of the foregoing and in accordance one aspect of the present invention, there is provided a testing device for testing an analyte in a sample of bodily fluid, comprising:

memory for storing data, said data being analyte data related to analyte measurements carried out by the meter and lifestyle data;

initiation means for initiating entry of data related to a specific category of lifestyle data;

navigation means for entry and navigation of said data; and transfer means for transferring said data to said memory.

Such a testing device provides simple and effective recordal of both analyte and lifestyle related data in a single, compact device. Input of lifestyle data can be initiated simply through use of the initiation means, without having to first perform an analyte measurement. Of course, it will be appreciated that the testing device could be used to measure only analyte levels, such as glucose levels for diagnosis and treatment of diabetes, without the added lifestyle functionality impinging on the usability of the testing device. Conversely, the testing device could also be used for diagnosis and treatment of diseases other than diabetes, either independently or in combination with diabetes tracking.

Preferably, the testing device comprises a display screen, wherein the transfer means is a processor, the processor being adapted to access the data stored in the memory and display said data on the display screen. The display screen may be a Liquid Crystal Display (LCD) screen able to render graphical objects in black and white, grayscale or colour. Improved chemiluminescence and/or a backlight provide visual enhancements over prior-art testing devices. Thus, use of the testing device is improved for individuals with impaired vision, which is particularly prevalent amongst people with diabetes.

Preferably, the processor is further adapted to perform an analysis on the data and display results of said analysis on the display screen.

Preferably, said analysis includes determining whether data lies outside a predetermined range. Such analysis allows simple self-diagnosis by an individual of their condition using the testing device, thereby increasing the individual's awareness of their condition and encouraging changes in their lifestyle, where required. Additional information may be immediately added following determination that data lies outside a predetermined range. This ensures that lifestyle information is entered in a timely and therefore accurate way.

In one embodiment of the present invention, said analysis comprises averaging data stored in the memory over a predetermined time period.

Preferably, said navigation means is adapted to select data for analysis or for display on the display screen.

Preferably, the analyte data includes a pointer to a bodily location from which an analyte sample was taken by an individual using the testing device. Thus, the accuracy and interpretation of measurements performed by the testing device can be improved. A user of the testing device or health care professional can more easily and accurately interpret the information provided in the data analysis performed by the testing device. Additionally, if a control solution is used as the analyte to be tested, the analyte data resulting from the testing of the control solution is flagged and such data is not used in any analysis of results performed by the testing device.

Preferably, said lifestyle data is stored in the memory as lifestyle records, each lifestyle record comprising:
  a date and time-stamp;
  a pointer to a lifestyle event; and
  a lifestyle value.

Preferably, said analyte data is stored in the memory as analyte records, each analyte record comprising:
  a date and time-stamp; and
  an analyte value;

Preferably, each analyte record further comprises:
  a pointer to a bodily location from which an analyte sample was taken by an individual using the testing device;
  a pointer to a lifestyle event; and
  a lifestyle value.

The time-stamp may be a multi-bit binary representation of the time and date for each record. The pointer to a lifestyle event may be a multi-bit binary value which corresponds to each specific type of quantifiable lifestyle data.

Preferably, said initiation means is a plurality of function-specific buttons, each function-specific button corresponding to a specific category of lifestyle data. Thus, entry of lifestyle data relating to a specific category of lifestyle data is quick and easy.

In view of the foregoing and in accordance a second aspect of the present invention, there is provided a testing device for testing an analyte in a sample of bodily fluid, comprising:
  memory for storing data;
  navigation means for entry and navigation of said data;
  transfer means for transferring said data to said memory; and
  user interface generation means for generating a user interface on a display screen, wherein:
  said data is analyte data related to analyte measurements carried out by the meter and lifestyle data;
  said lifestyle data is arranged into one or more categories of lifestyle data;
  said user interface has sub-category options for each category of lifestyle data;
  said navigation means is adapted to select said sub-category options;
  said user interface generation means is responsive to selection of a given sub-category option, such that value options for each of said sub-category options are displayed in the user interface;
  said navigation means is adapted to select said value options;
  said user interface generation means is responsive to selection of a value option, such that values for the selected value options are displayed in the user interface;
  said navigation means is adapted to select said values; and
  said transfer means is responsive to selection of said values for transferring one or more selected values into said memory.

A standard data entry approach for all types of lifestyle data is thus achieved, making the user interface easy to use and entry and manipulation of lifestyle data simple for an individual not familiar with such testing devices or for someone who is only uses the testing device occasionally. This way, use of the testing device for entry of lifestyle data is also encouraged.

Preferably, the transfer means further transfers into said memory with said one or more selected values:
  a time-stamp; and
  a pointer to the selected value option.

Preferably, the user interface generation means is responsive to said navigation means, such that selectable categories of said data are displayed in the user interface, said navigation means being adapted to select said selectable options, the user interface generation means being responsive to selection of one of said selectable categories to display on the display screen data from the memory corresponding to a selected category of said data.

Preferably, the testing device further comprises analysis means for performing an analysis on said data, wherein analysis options for each selectable category are displayed in the user interface, said navigation means being adapted to select said analysis options, the analysis means being responsive to selection of one of said analysis options to analyse said data stored in the memory, the user interface generation means being responsive to said analysis means to display results of said analysis on the display screen. The results of said analysis may be displayed graphically on the display screen, for example, as graphs of different types of stored data against time.

Preferably, said analysis comprises averaging said data stored in said memory over a predetermined time period, said predetermined time period being determined by selection of one of said analysis options.

Preferably, the testing device further comprises one or more function-specific buttons, wherein:
  each function-specific button corresponds to an associated category of lifestyle data; and
  the user interface generation means is responsive to operation of one of the function-specific buttons to immediately display said sub-category options for the associated category of lifestyle data in the user interface. Thus, entry of lifestyle data relating to a specific category of lifestyle data is quick and simple.

Preferably, said categories of lifestyle data comprise:
a food category relating to food intake of an individual;
a medication category relating to medication use of an individual;
a health category relating to health check-ups, health test results and/or health condition of an individual; and
an exercise category relating to exercise levels of an individual.

In accordance with a third aspect of the present invention, there is provided a testing device for testing an analyte in a sample of bodily fluid, comprising:
memory for storing data, said data being analyte data related to analyte measurements carried out by the testing device and lifestyle data;
navigation means for entry and navigation of said data;
transfer means for transferring said data to said memory; and
prompt means for prompting a user of the testing device to enter lifestyle data associated with an analyte measurement following a carrying out of said analyte measurement, if said analyte measurement lies outside a pre-defined range.

Preferably, there is further provided a display screen and the prompt means is adapted to display messages on the display screen, said messages prompting a user of the testing device to enter lifestyle data associated with said analyte measurement.

Preferably, said transfer means is a processor and said processor is adapted to perform an analysis on selected lifestyle data and/or analyte data and display results of said analysis on the display.

In accordance with a fourth aspect of the present invention, there is provided a testing device for testing an analyte in a sample of bodily fluid, comprising:
memory for storing analyte data; and
navigation means,
wherein:
said sample of bodily fluid is usually obtained from a specific bodily location on an individual; and
said navigation means is adapted to flag analyte data stored in the memory if said sample of bodily fluid is obtained from an alternate bodily location other than said specific bodily location following a carrying out of an analyte measurement.

Preferably, said navigation means is further adapted to indicate to the memory said alternate bodily location, such that a pointer to said alternate location is stored with associated analyte data in the memory.

In one embodiment of the present invention, there is further provided a display screen, and said navigation means comprises a cursor button and an OK button, such that operation of the cursor button adapts the display screen to display one or more alternate bodily location options corresponding to one or more alternate bodily locations and operation of the OK button sends said alternate bodily location to the memory.

In accordance with a fifth aspect of the present invention, there is provided a testing device for testing an analyte in a sample of bodily fluid, comprising:
memory adapted for storing data, said data being analyte data and lifestyle data;
a display screen;
a processor adapted to access said data and display said data on the display screen; and
navigation means adapted to be operated to select said data to be accessed by the processor.

Preferably, the processor is further adapted to perform an analysis on selected data and display results of said analysis on the display screen.

Preferably, the navigation means is one or more navigation buttons.

Preferably, the navigation buttons consist of a cursor button, an OK button and a back button.

In one embodiment of the present invention, there is provided communication means adapted to transfer data between said memory and an external device. Thus, diagnosis and treatment of an individual using the testing device is improved. In fact, the use of a personal computer allows diagnosis and prescription of treatment from a remote location, since data stored in the testing device may be transferred from the testing device and transmitted, optionally via the Internet, to a physician anywhere in the world.

Preferably, the testing device is a glucose meter and one of the analytes being tested is glucose. Thus, diagnosis and treatment of diabetes in an individual using the testing device is improved.

In accordance with a sixth aspect of the present invention, there is provided a method of storing lifestyle data related to the lifestyle of an individual in a testing device for testing an analyte in a sample of bodily fluid, comprising the steps of:
indicating a specific category of lifestyle data to the testing device;
indicating a sub-category of lifestyle data to the testing device;
inputting a value into the testing device; and
storing the value in memory in the testing device.

In accordance with a seventh aspect of the present invention, there is provided a method of manipulating lifestyle data related to the lifestyle of an individual and analyte data stored in a testing device for testing an analyte in a sample of bodily fluid, said method comprising the steps of:
indicating a category of data to the testing device;
analysing data from said category of data, thereby generating analytical results; and
displaying said analytical results on a display screen on the testing device.

Preferably, the method further comprises the step of indicating a time period for analysis of said data before analysing said data, the step of analysing data comprising averaging data from said category of data over said time period.

In accordance with an eighth aspect of the present invention, there is provided a method of storing analyte data in a testing device for testing an analyte in a sample of bodily fluid, said method comprising the steps of:
obtaining a sample of bodily fluid from a bodily location, said sample of bodily fluid normally being obtained from a specific bodily location on an individual;
measuring an analyte level in the sample of bodily fluid;
storing said analyte level in memory in the testing device; and
flagging said analyte level in the memory if said sample of bodily fluid was obtained from an alternate bodily location other than said specific bodily location.

Preferably, the step of flagging said analyte level in the memory comprises storing a pointer to said alternate bodily location with said analyte level in the memory.

The present invention provides a testing device for sampling and performing an analysis on a sample of bodily fluid, such as blood, and storing the results of said analysis, including means for inputting and storing inputted lifestyle data.

The present invention facilitates the monitoring of an individual's lifestyle by integrating into a single device the steps involved in sampling and analysing blood and recording other information about an individual's everyday life into a simple process employing a single device.

BRIEF DESCRIPTION OF DRAWINGS

A specific embodiment is now described by way of example only and with reference to the accompanying drawings, in which.

DETAILED DESCRIPTION OF DRAWINGS

The present invention will be described below relative to an illustrative embodiment. Those skilled in the art will appreciate that the present invention may be implemented in a number of different applications and embodiments and is not specifically limited in its application to the particular embodiment depicted herein. In particular, the present invention will be discussed below in connection with sampling blood, although those of ordinary skill will recognise that the device could be modified to be used with other types of fluids or analytes besides glucose.

Figure 1:
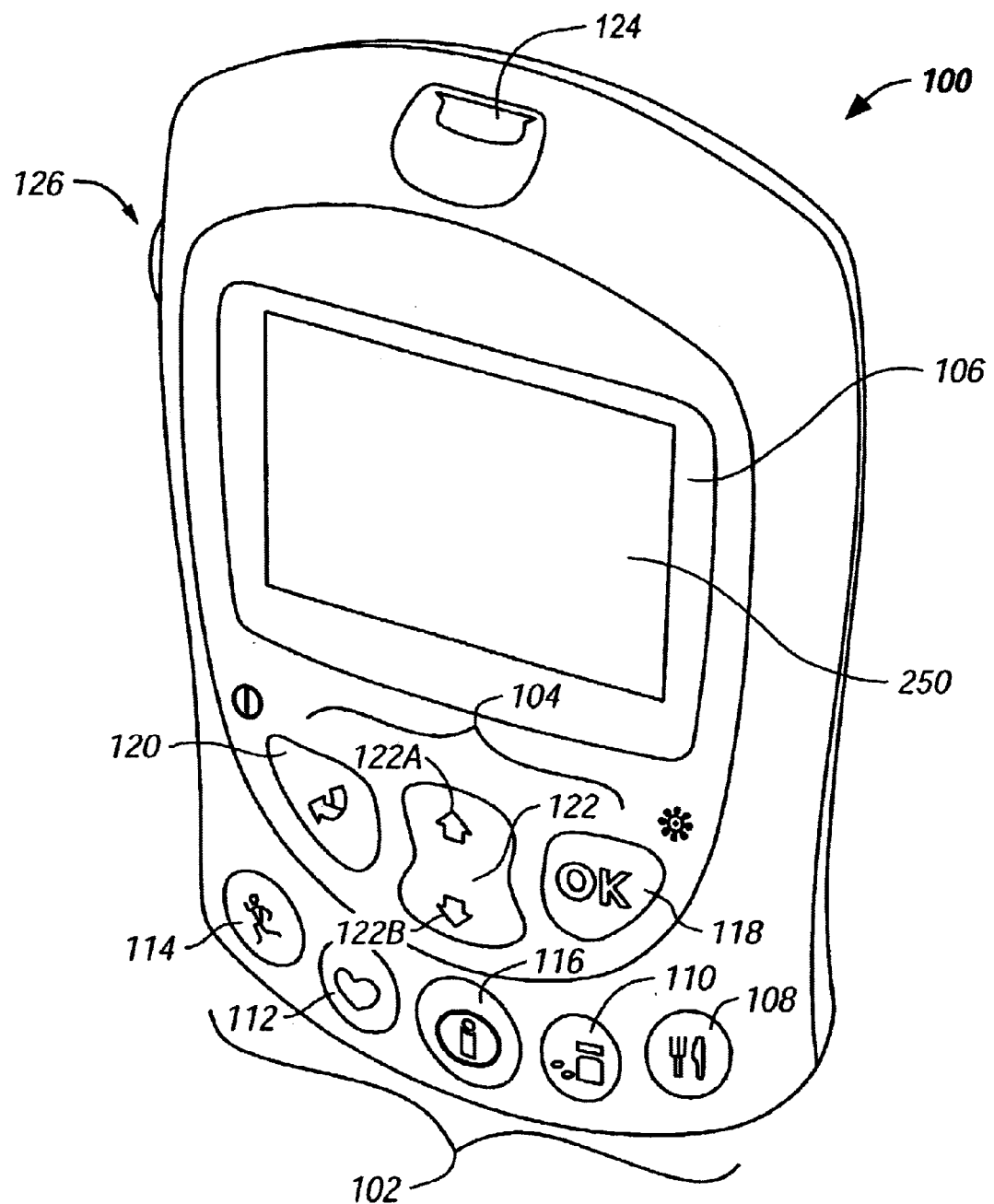
FIG. 1 is a three-dimensional representation of the testing device according to one embodiment of the present invention.

Referring to FIG. 1, there is shown a testing device (100) for testing glucose levels in the blood of an individual. The testing device (100) externally includes initiation means (102) for initiating entry of data related to a specific category of lifestyle data, specifically function-specific buttons (108, 110, 112, 114), and navigation means (104) for entry and navigation of data, specifically navigation buttons (118, 120, 122). Lifestyle data is any information which is related to the everyday lifestyle of an individual. In the embodiment shown in FIG. 1, lifestyle data is divided into four categories, namely food, medication, health and exercise categories, which relate respectively to food intake, medication use, the occurrence of health check-ups and general health condition and exercise levels of an individual. Further included on the testing device is a liquid crystal display screen (106) for displaying measured glucose levels and facilitating entry of lifestyle related information into the testing device (100).

Each category of lifestyle data has an associated function-specific button, operation of which immediately initiates a sequence for entry of data corresponding to the category of lifestyle to which the operated function-specific button relates. The categories to which each of the function-specific buttons (102) relate are shown on the surface of the function-specific buttons (102) by a graphical representation. The food category is represented on a food function-specific button (108) by a conventional "knife and fork" icon. There are similar suitable representations on a medication function-specific button (110), health function-specific button (112) and an exercise function-specific button (114). In an alternative embodiment, the function-specific buttons may have tactile icons on their surfaces, such tactile icons facilitating operation of the testing device by partially sighted or blind individuals. Operation of one of the function-specific buttons (102) when the testing device (100) is switched off, immediately switches the testing device on and initiates a sequence for entry of data.

The function-specific buttons (102) ensure that a user of the testing device (100) does not need to navigate through a complex and unfamiliar menu system to enter lifestyle data. Instead, to immediately enter an applicable data entry sequence, a user merely needs to press one of the function-specific buttons (102). The required function specific-button is easily determinable from the graphical icon on the button's surface. An information button (116) is another function-specific button, but it does not relate to a specific category of lifestyle data. Instead, pressing the information button (116) immediately allows a user to view and analyse data stored in the testing device (100). Such data may be any data stored in the testing device (100), for example previously measured glucose levels or entered lifestyle information.

The navigation buttons (104) comprise an OK button (118), a back button (120) and a cursor button (122) and facilitate entry and analysis of data stored in the testing device by enabling a user to navigate through a user interface (250) displayed on the display screen (106). The cursor button is bi-directional and has an upwards operative section (122a) and a downwards operative section (122b).

The testing device (100) is switched on by pressing any one of the function-specific buttons (102) or the back button (120). In addition, the testing device (100) is automatically switched on when a test-strip is inserted into test-strip port (124) for measurement of a glucose level in a sample of blood placed on the test-strip. The testing device (100) can be switched off by holding down the back button (120) for a pre-defined period of time. The display screen of the testing device (106) includes a backlight, which can be switched on or off by holding down the OK button (118) for a pre-defined period of time.

Additionally, there is a communication port (126) on one side of the testing device (100) which accepts a connector attached to a connecting lead, thereby allowing the testing device (100) to be linked to an external device such as a personal computer. The personal computer, running appropriate software, allows entry and modification of set-up information (e.g. the current time and date and language), as well as being able to perform other analysis and display functions performed by the testing device (100). In addition, the personal computer may be able to perform advanced analysis functions or transmit transferred data to another personal computer, optionally via the Internet, for improved diagnosis and treatment at a remote location. This way, improved treatment and diagnosis of diabetes by a medical practitioner is facilitated by being able to link the testing device (100) with the personal computer.

Figure 2A:
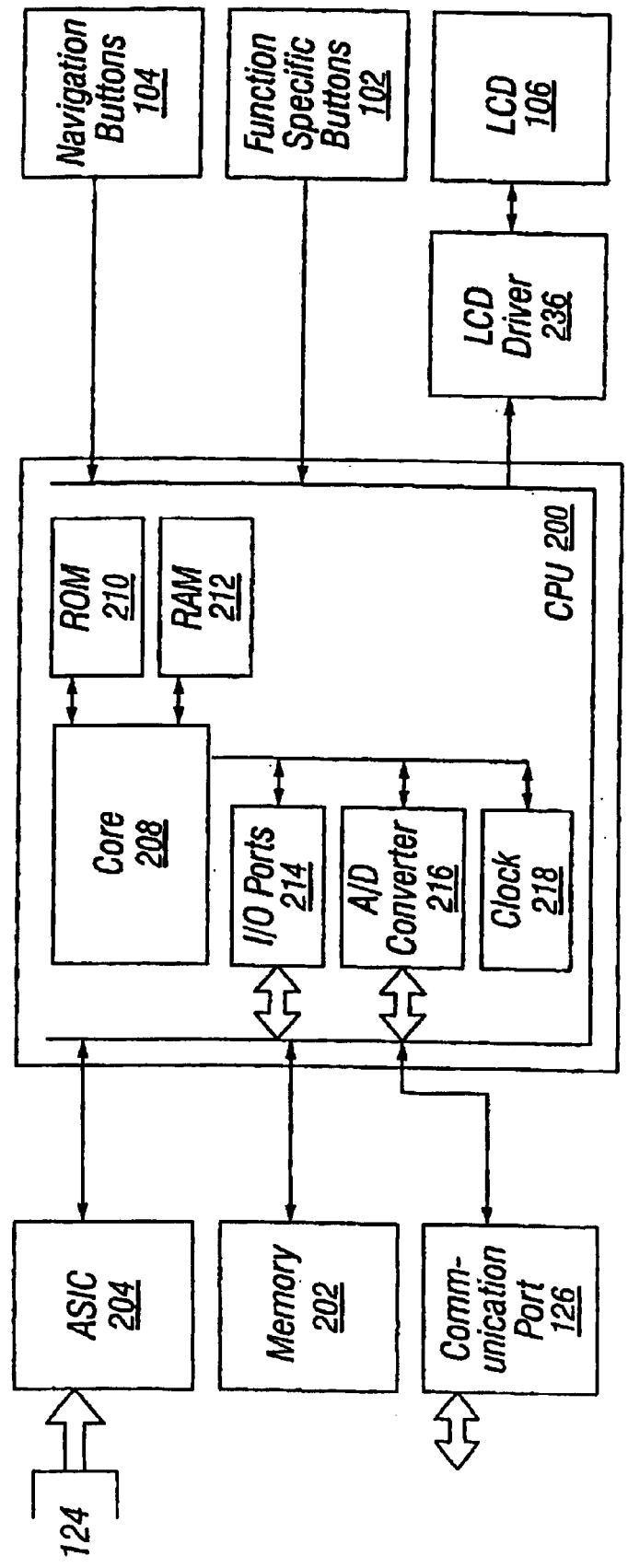
FIG. 2a is a block diagram of the principal internal components of the testing device of FIG. 1.

Referring to FIG. 2a, the internal layout of the testing device (100) is shown. Internally, the testing device comprises a processor (200), which, in the testing device of FIG. 1, is a 32-bit RISC microcontroller. The processor is bi-directionally connected via I/O ports (214) to memory (202), which, in the testing device of FIG. 1, is an EEPROM. Also connected to the processor (200) via I/O ports (214) are the communication port (126), the navigation buttons (104), the function-specific buttons (102) and a display screen driver (236). The communication port (126) is serially connected to the processor (200), thereby enabling transfer of data between the memory (202) and an external device, such as a personal computer. The navigation buttons (104) and the function-specific buttons (102) are directly connected to the processor (200). The processor (200) controls the display screen (106) via the display screen driver (236).

An Application Specific Integrated Circuit (ASIC) (204) implements electronic circuitry required to facilitate measurement of a glucose level from a sample of blood on a test-strip inserted into the test-strip port (124). For the purpose of internal crosschecking, analogue voltages can be supplied to the ASIC (204) and measured from the ASIC (204) by the processor (200) through an internal A/D converter (216).

The processor (200) further comprises internally: a processor core (208), a ROM (210) containing computer code, RAM (212) and a clock (218), which provide control circuitry for components, which are connected externally to the processor (200) to the I/O ports (214) and the A/D converter (216).

Figure 2B:
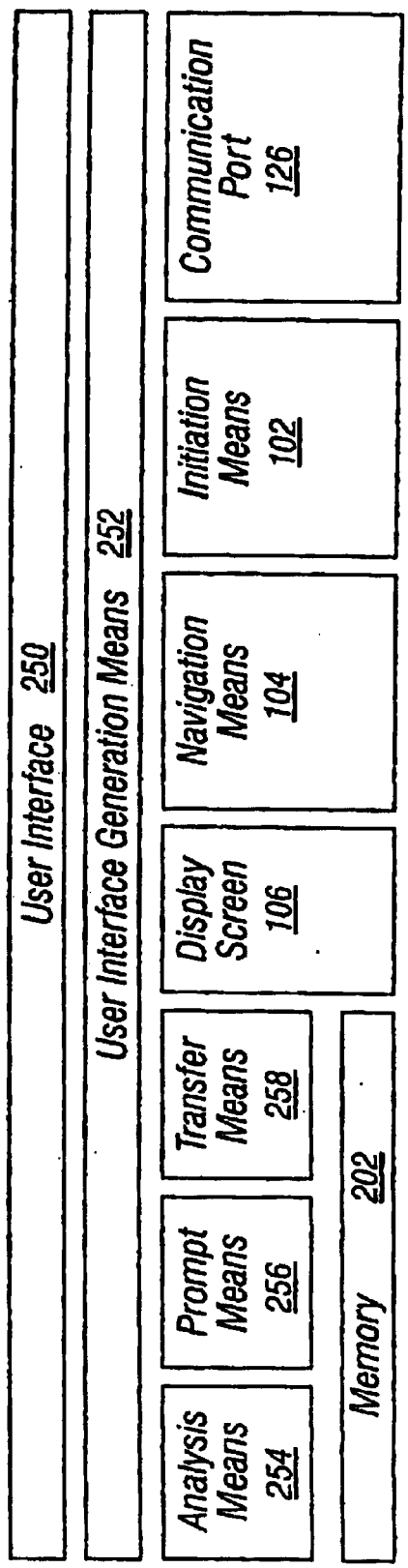
FIG. 2b shows a layer structure of functional components of the testing device of FIG. 1.

Referring to FIG. 2b, a layer structure of the functional aspects of the testing device (100) is shown. User interface generation means (252) generates a user interface (250) on the display screen (106) of the testing device (100). The navigation means (104) (specifically the navigation buttons (104) in the described embodiment) and the initiation means (102) (specifically the function-specific buttons (102) in the described embodiment) allow a user to interact with the user interface (250). Transfer means (258), on instruction from the user interface generation means (252), transfers data stored in the memory (202) back to the user interface generation means (252) for display in the user interface (250). Analysis means (254), under instruction from the user interface generation means (252), performs an analysis on data stored in the memory (202) and returns results of the analysis to the user interface generation means (252) for display in the user interface (250). When measured glucose levels are outside a pre-defined range, prompt means (256) instructs the user interface generation means (252) to display a message prompting a user of the testing device (100) to enter lifestyle data following measurement of a glucose level from a sample of blood on a test strip inserted into the testing device (100).

Figure 3:
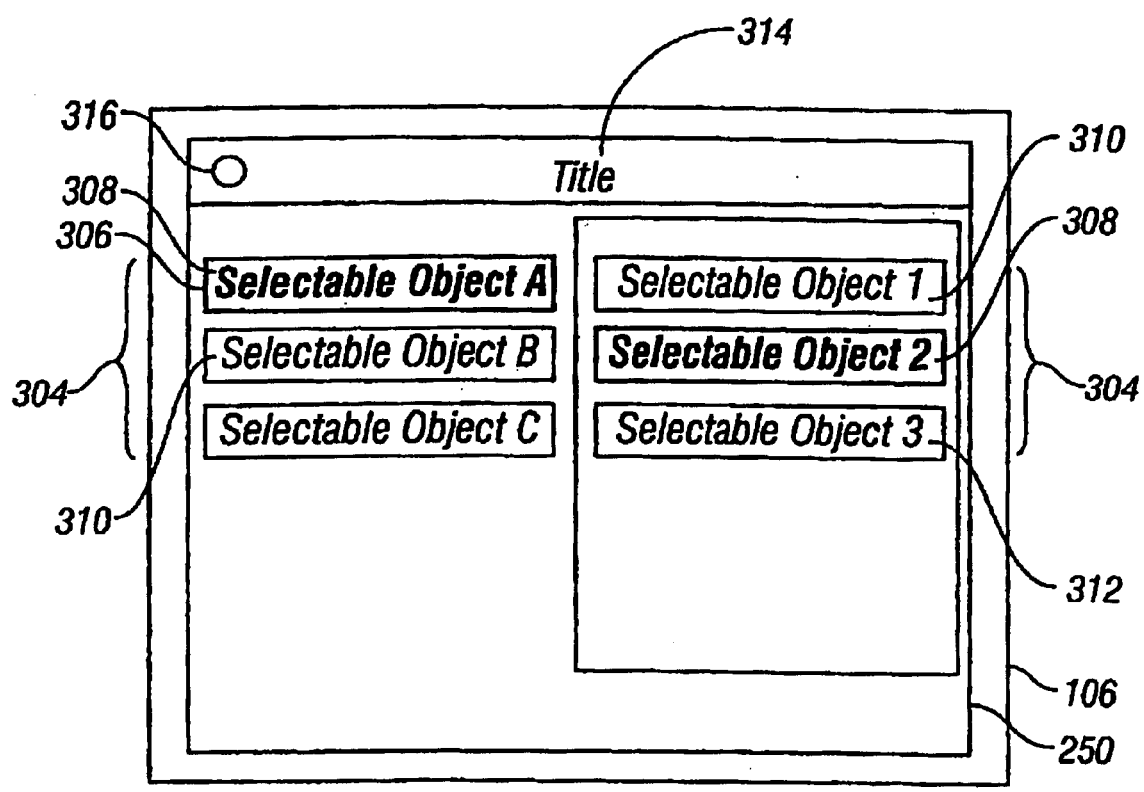
FIG. 3 is a generic representation of a user interface displayed on a display screen of the testing device of FIG. 1.

FIG. 3 shows a generic user interface (250) generated by the user interface generation means (252) and displayed on the display screen (106). Selectable objects (304) are displayed in the user interface (250). The user interface generation means (252) adapts the user interface (250) on operation of the navigation means (104), which in the presently described embodiment, are the navigation buttons (104).

The selectable objects (304) are highlighted by operating the cursor button (122). The user interface generation means (252) adapts the user interface (250) such that the selectable objects (304) are highlighted in turn. In the embodiment shown, the selectable objects (304) are highlighted by a highlight bar (306), which inverts the contents of a rectangular area surrounding a highlighted selectable object (308). A title (314) and a graphical icon (316) related to the most recently operated function-specific button (102) are displayed in the user interface (250). Both the title (314) and the graphical icon (316) correspond to the current screen being displayed in the user interface (250). Operation of the cursor button (122) on its upwards or downwards operative section (122a, 122b) will move the highlight bar (306) up or down through the selectable objects (304) respectively. However, it will be readily appreciated that a selectable object (308) could also be considered as highlighted by being the only selectable object (308) displayed in the user interface (250) at a given time. In such a case, operation of the cursor button (122) on its upwards or downwards operative section (122a, 122b) would cause the user interface generation means (252) to adapt the user interface (250) so that the current highlighted selectable object (308) becomes hidden and either the previous or next selectable object (312, 310) is displayed. The highlighted selectable object (308) is selected by activating the OK button (118).

In general navigation of the user interface (250) described herein, operation of the back button (120), unless otherwise specified, generally causes the user interface generation means (252) to return the user interface (250) to a previous state of the user interface (250), prior to the previous operation of the OK button (118), thereby ensuring data stored in the memory (202) remains unchanged from its state prior to operation of the OK button (118).

Figure 4:
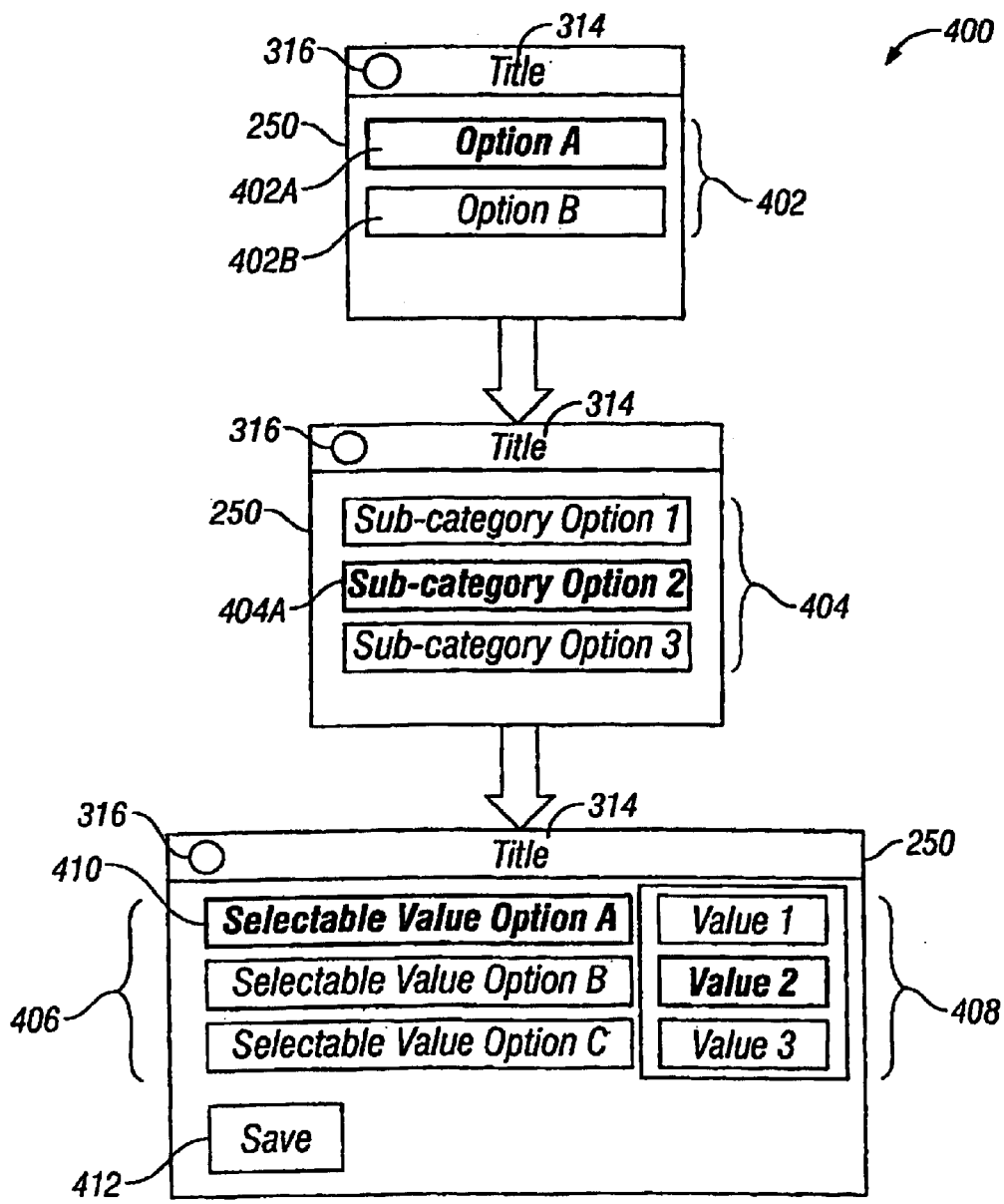
FIG. 4 is a representation of a generalised lifestyle data entry sequence employed by the testing device of FIG. 1.

Referring to FIG. 4, activation of one of the function-specific buttons (102) relating to a specific category of lifestyle data starts a lifestyle data entry sequence (400) for the specific category of lifestyle data. A generalised lifestyle data entry sequence (400) is described below with reference to FIG. 4.

For each category of lifestyle data, the user interface generation means (252) generates a user interface (250) to query whether the current lifestyle data being input is for the present time and date or for another time and date. Two selectable objects (304), namely time options (402) are displayed in the user interface (250). Option A (402a) shows the current time and date and option B (402b) displays the message "Other time". Throughout the lifestyle data entry sequence (400), a title (314) and a graphical icon (316), both corresponding to the category of lifestyle data selected by operation of one of the function specific buttons (102), are shown in the user interface (250). Thus, a user of the testing device (100) can immediately recognise whereabouts in the user interface (250) they are. Hence, ease of use and navigation of the user interface (250), especially in combination with operation of the back button (120), is improved.

If option A (402a) is selected, the current date and time is used as time and date information for storing with lifestyle data entered in the current lifestyle data entry sequence (400).

If option B (402b) is selected, the user interface generation means (252) starts a date and time selection sequence to set the time and date information for storing with lifestyle data entered in the current lifestyle data entry sequence (400). The date and time selection sequence comprises: the user interface generation means (252) displaying selectable dates on the display screen (106), selection of a date, the user interface generation means (252) then displaying selectable times of day on the display screen (106) and selection of a time of day for entry of lifestyle data.

Following selection of the date and time information, the user interface generation means (252) modifies the user interface (250) to display selectable objects (304) which are selectable sub-category options (404) for each category of lifestyle data. The user interface generation means (252) is responsive to selection of one of the selectable sub-category options (404), such that a further set of selectable objects, specifically selectable value options (406), which are appropriate for a selected sub-category option (404a), are displayed in the user interface (250). It will be appreciated that the selectable value options (406) can be displayed alongside the selectable sub-category options (404) or in a separate screen in the user interface (250) entirely.

On selection of a highlighted selectable value option (410), selectable values (408), which may be numerical or descriptive, can be viewed and selected as described above. The selectable values (408) are shown either alongside the selectable value options (406), as shown in FIG. 3, or in a separate screen in the user interface (250). Operation of the back button (120) allows a user to highlight other selectable value options (406), without a selectable value being selected for the current selected sub-category option (404a). Once all desired selectable value options have been selected (i.e. an entire list of selectable value options has been scrolled through or had values entered), the transfer means (258), which is responsive to the user interface generation means (252), recognising that the OK button (118) has been operated, transfers one or more values (408) for the given sub-category of lifestyle data directly into the memory (202) of the testing device (100). Optionally, there may be a dedicated "Save" selectable value option (412), selection of which immediately transfers one or more values (408) for the given sub-category of lifestyle data directly into the memory (202) of the testing device (100). If one or more values, which are descriptive, have been entered, then a numerical value acting as a pointer to the descriptive value is transferred into the memory (202).

One of the sub-category options (404), value options (410) and/or values (408) may labelled "------", selection of which skips entry of data for the selected lifestyle category, sub-category option or value option respectively by inserting a null value into the memory (202). Thus, there is a common approach for entry and editing of data in different lifestyle categories, which all have different sub-categories and support different types of data. Hence, it is easy to learn how to use the testing device (100) for manipulation and viewing of different types of data.

Figure 5A:
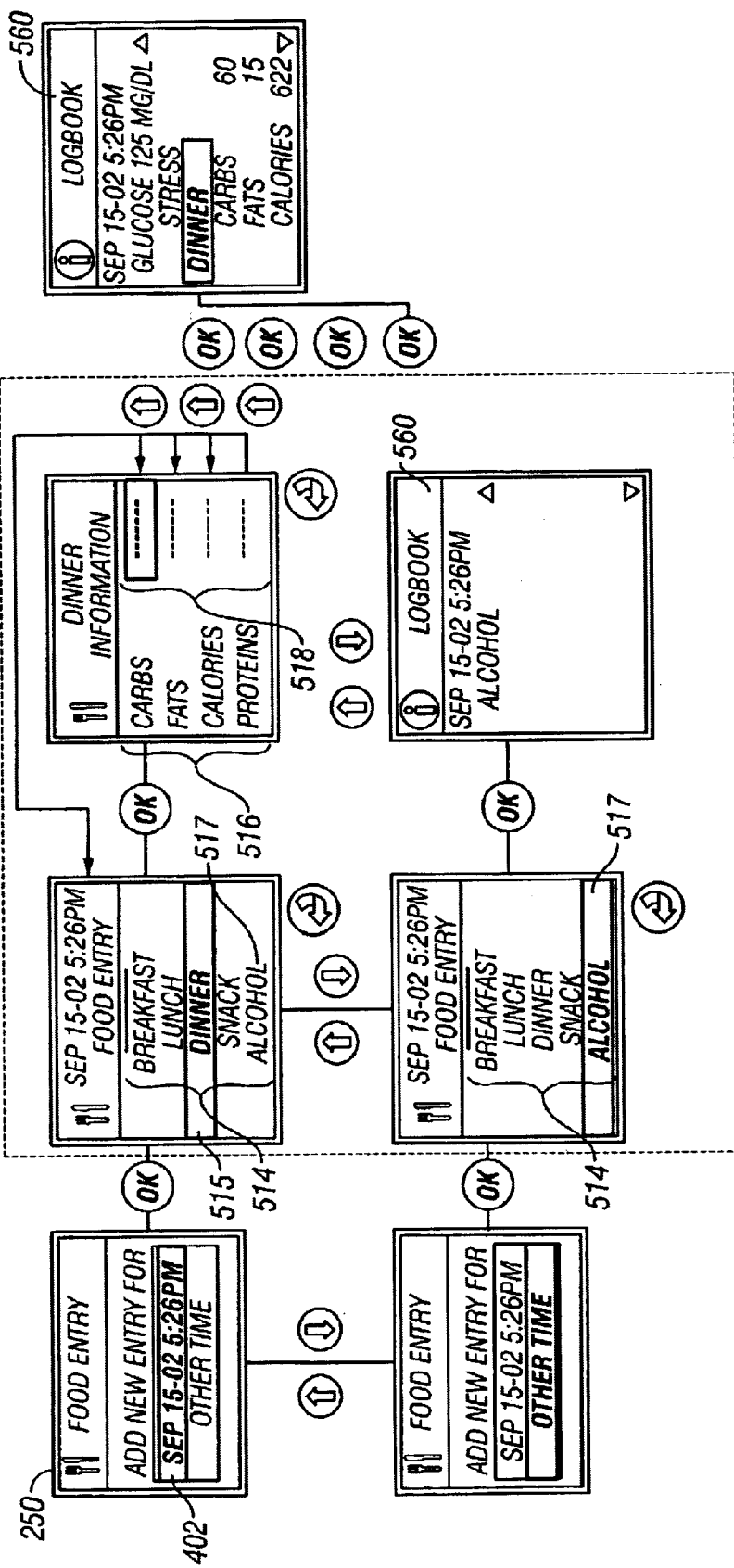
FIGS. 5a to 5d show specific data entry sequences for entry of food, medication, health and exercise related lifestyle data according to the generalised lifestyle data entry sequence of FIG. 4.

Referring to FIG. 5a, the generalised lifestyle data entry sequence (400) is now described in detail specifically in relation to entry of lifestyle data in the food category. Upon operation of the food function-specific button (108), the time options (402), as described above, are displayed in the user interface (250). Having selected the time and date, food sub-category options (514), specifically labelled "Breakfast", "Lunch", "Dinner", "Snack" and "Alcohol" are displayed in the user interface (250) for selection. One of the food sub-category options is labelled "------", selection of which skips entry of data and displays a logbook (560) in the user interface (250) (see below). On initial display of the food sub-category options (514), a default food sub-category option (515) is highlighted, the default food sub-category option (515) being determined by comparing pre-defined meal times with the current time. Thus, the user interface (250) provides for intelligent interaction between a given user and the testing device (100).

Selection of one of the food sub-category options (514), corresponding to "Breakfast", "Lunch", "Dinner" and "Snack" displays selectable food value options (516) in the user interface (250) labelled "Carbs", "Fats", "Calories" and "Proteins", relating to carbohydrate, fat, calorific energy and protein intake. Each of the selectable food value options (516) can be highlighted in turn by operation of the cursor button (122) and selected by operation of the OK button (118). Food values (518) can be entered for one or more of the selectable food value options (516) (as described above). Any food values (518) that are selected and entered are stored in the memory (202) following entry of the last of the food values (518) (i.e. the food value relating to protein intake).

Selection of the "Alcohol" food sub-category option (517) immediately transfers a pointer corresponding to a unit of alcohol consumption into the memory (202), without displaying selectable value options (516) in the user interface (250).

Following entry of lifestyle data for the food category, the logbook (560) (see below) is displayed in the user interface (250).

Figures 2, 5B:
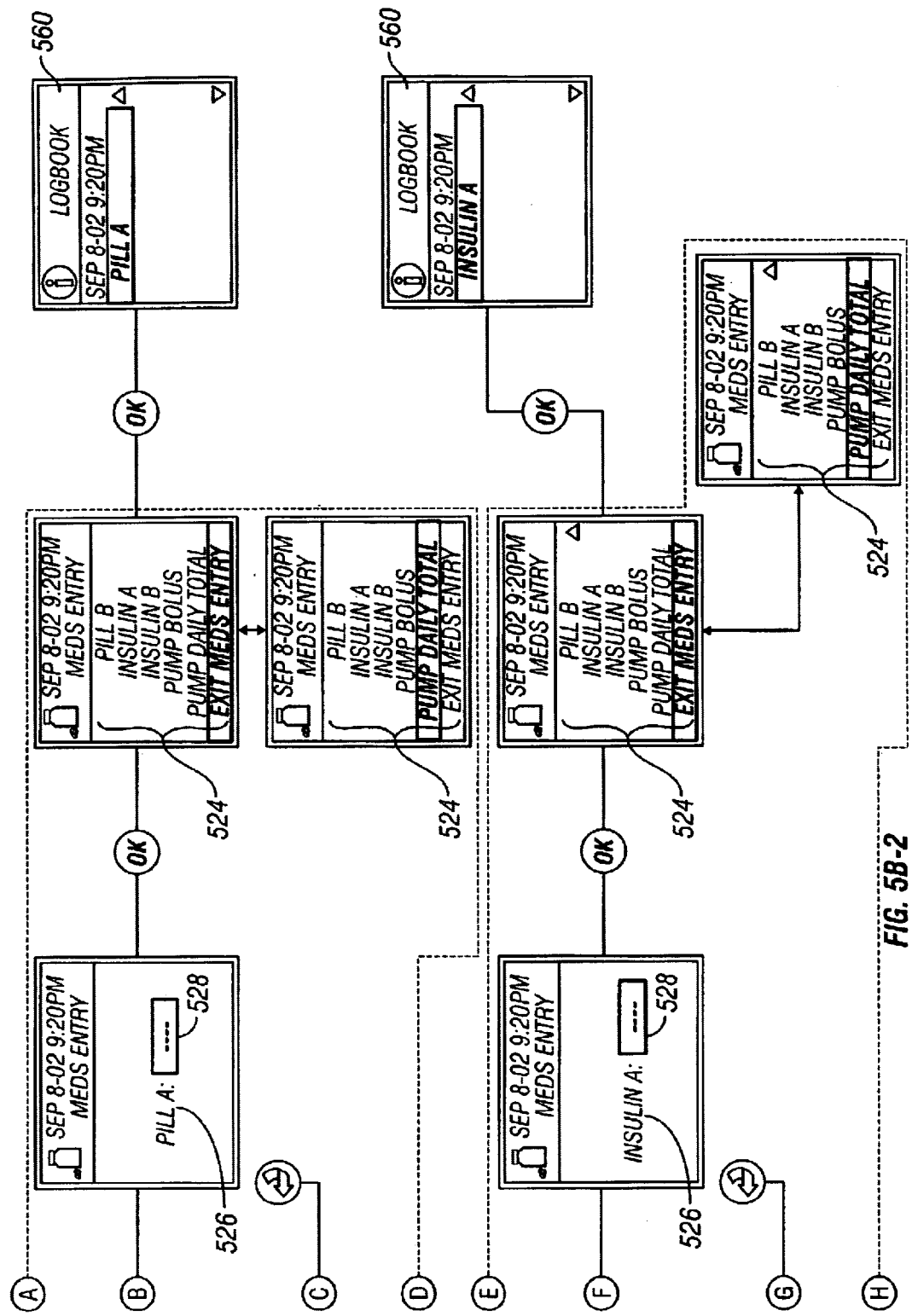

Referring to FIG. 5b, the generalised lifestyle data entry sequence (400) is now described in detail specifically in relation to entry of lifestyle data in the medication category. Upon operation of the medication function-specific button (110), the time options (402), as described above, are displayed in the user interface (250). Having entered the time and date information, medication sub-category options (524), nominally labelled "Pill A", "Pill B", "Insulin A", "Insulin B", "Pump Bolus" and "Pump Daily Total" are displayed in the user interface (250) for selection. One of the medication sub-category options (524) is labelled "Exit Meds Entry", selection of which skips the entry of data and displays the logbook (560) in the user interface (250) (see below). Some of the aforementioned medication sub-category options (524) are customisable through a set-up sequence (described below) and need not necessarily relate to medication which is specifically for treatment of diabetes.

Selection of one of the medication sub-category options (524) displays one or more selectable medication value options (526) in the user interface (250). Each of the selectable medication value options (526) can be selected by operation of the OK button (118) so that medication values (528) can be highlighted and selected for one or more of the selectable medication value options (526) corresponding to one of the selected medication sub-category options (524). Entered medication values (528) are stored in the memory (202) with a pointer to the selected medication sub-category and the time and date information.

Previously selected medication values (528) are used as default medication values, in that a previously entered medication value for a given selectable medication value option and a given time of day (as specified in a set-up sequence of the testing device (see below)) becomes the medication value which is initially highlighted upon selection of a given selectable medication value option (526). Thus, the user interface (250) provides for intelligent interaction between a given user and the testing device (100). Additionally, use of the cursor key (122) is minimised. Accordingly, the general usability of the testing device (100) is improved.

Figures 1, 5C:
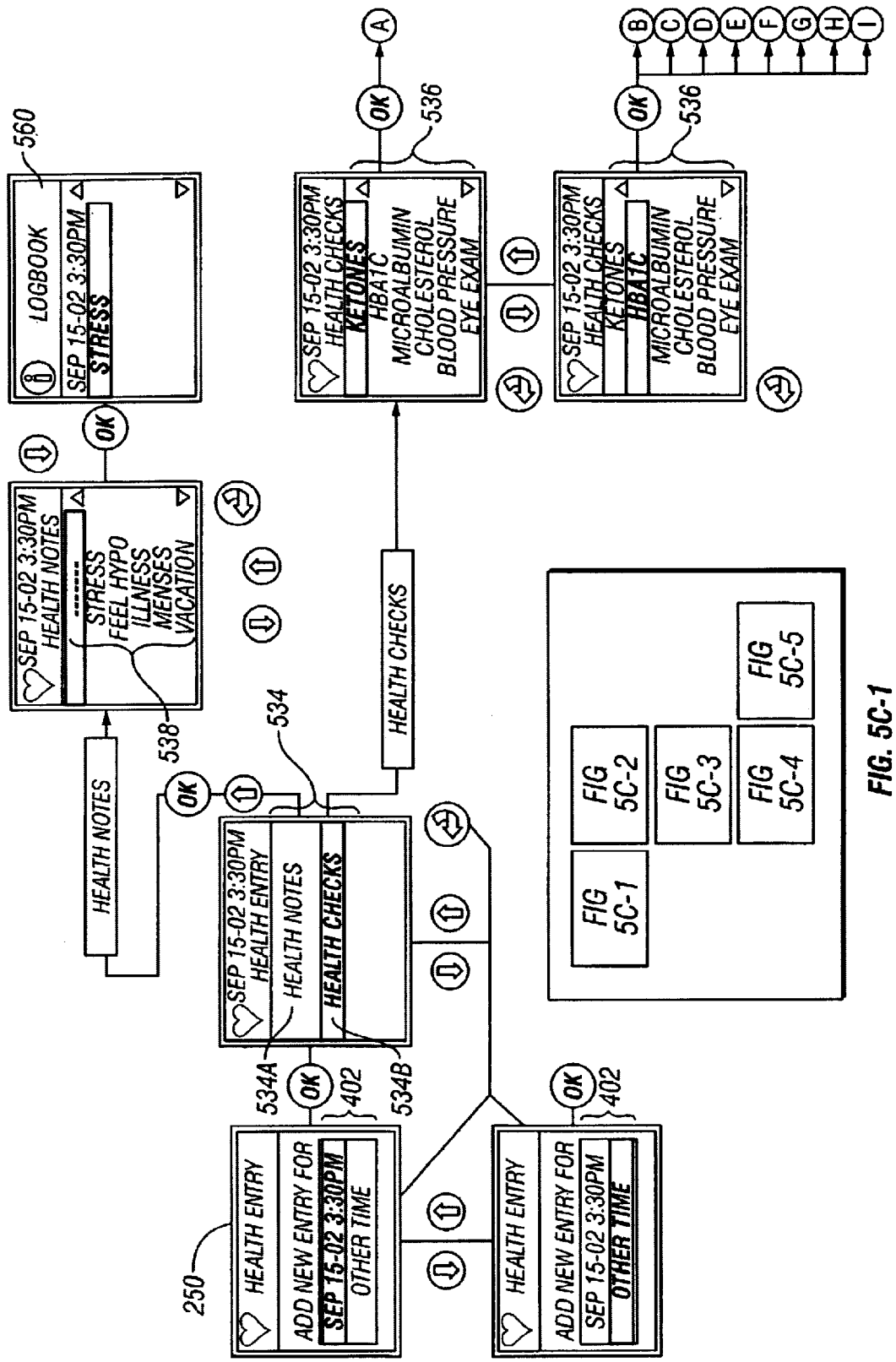
Figures 2, 5C:
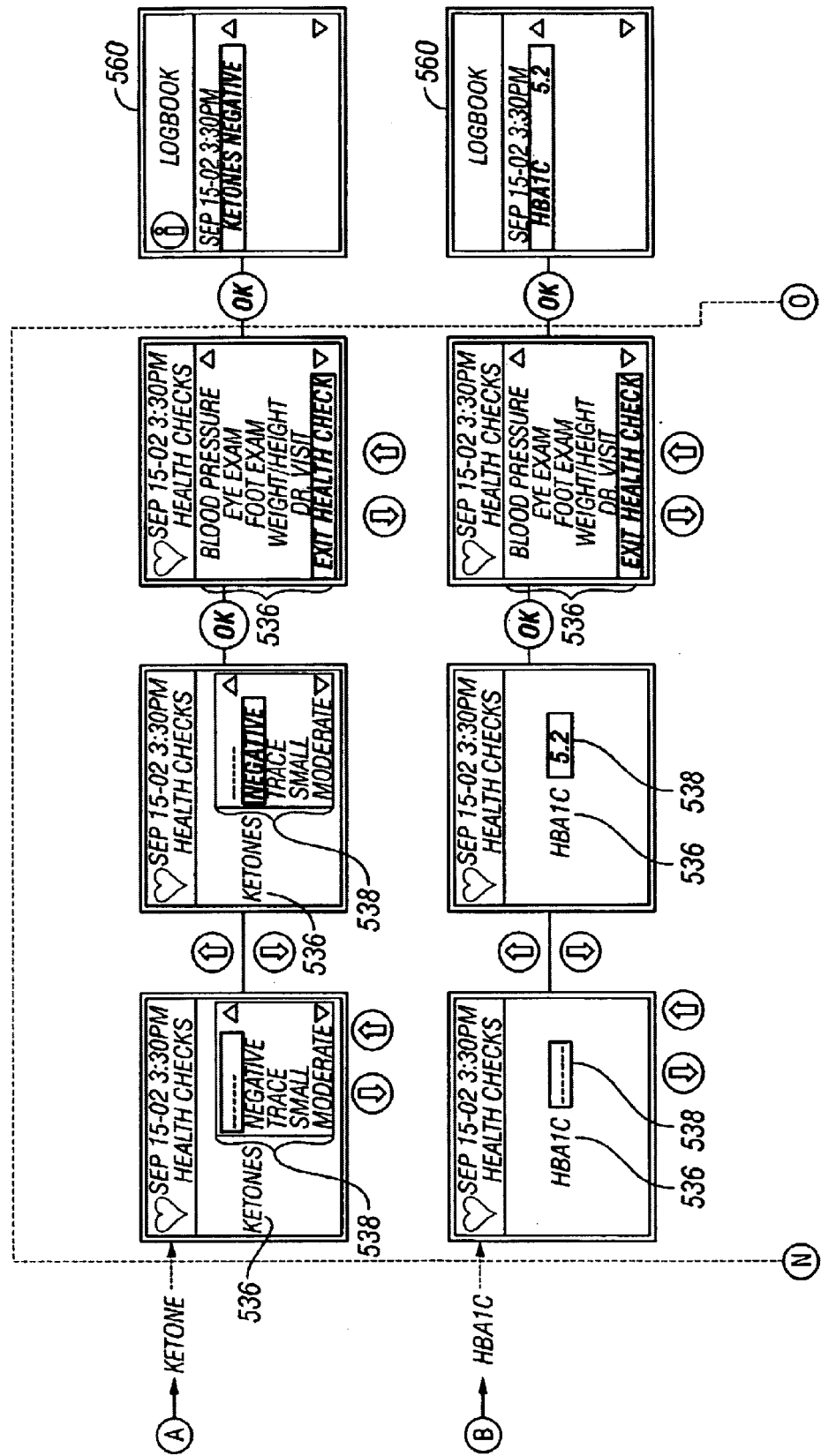
Figures 3, 5C:
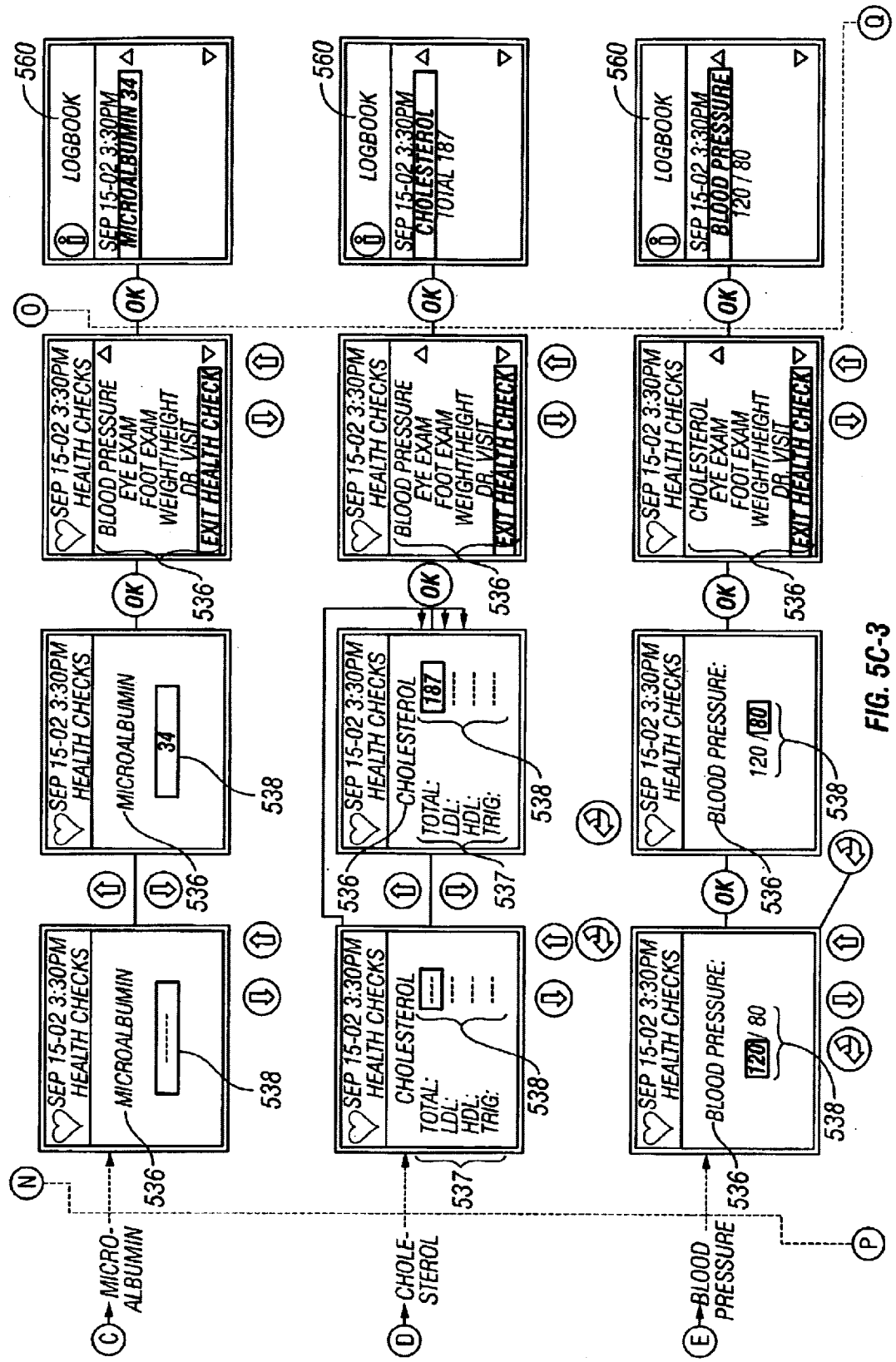
Figures 4, 5C:
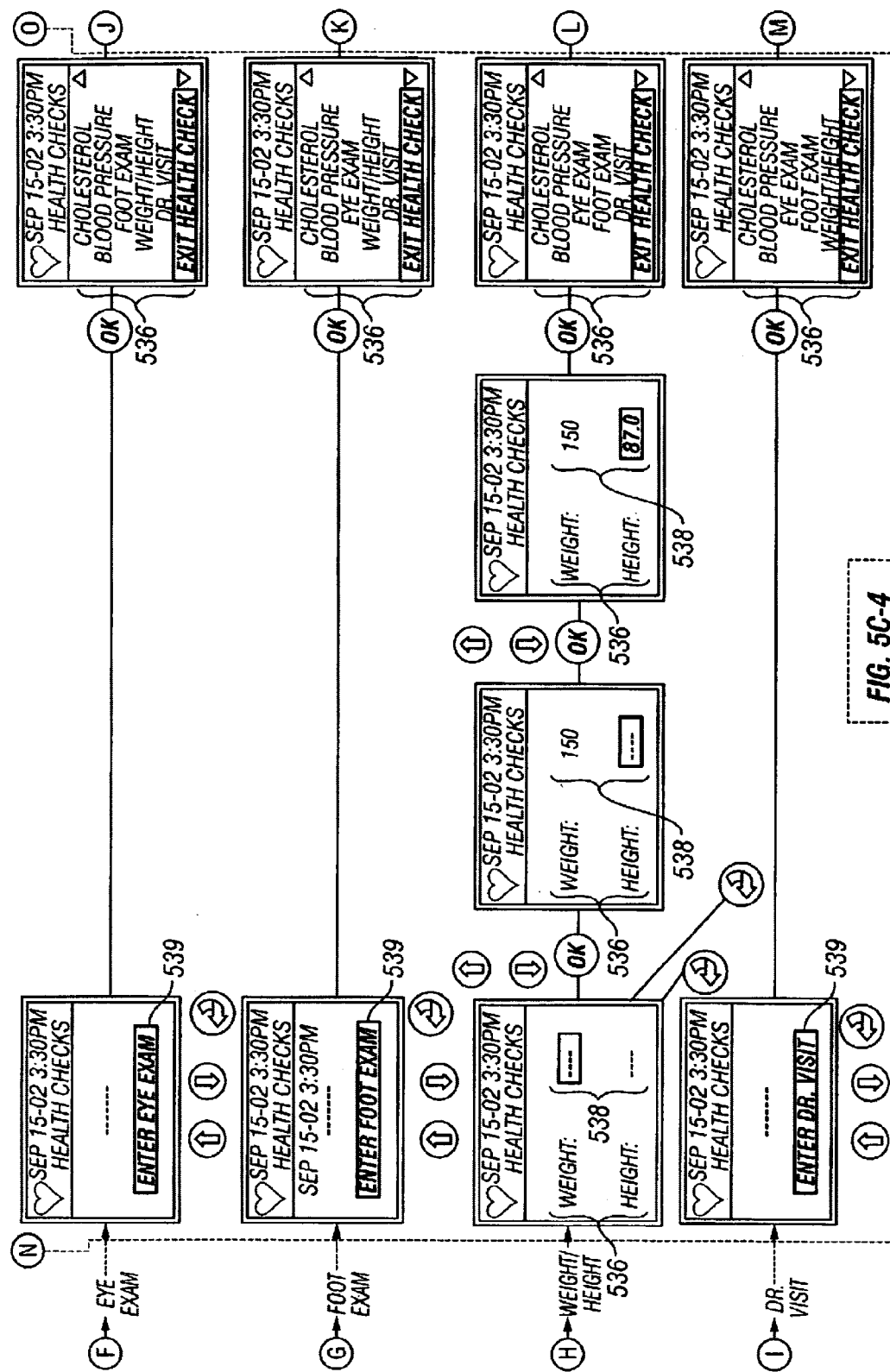
Figures 5, 5C:
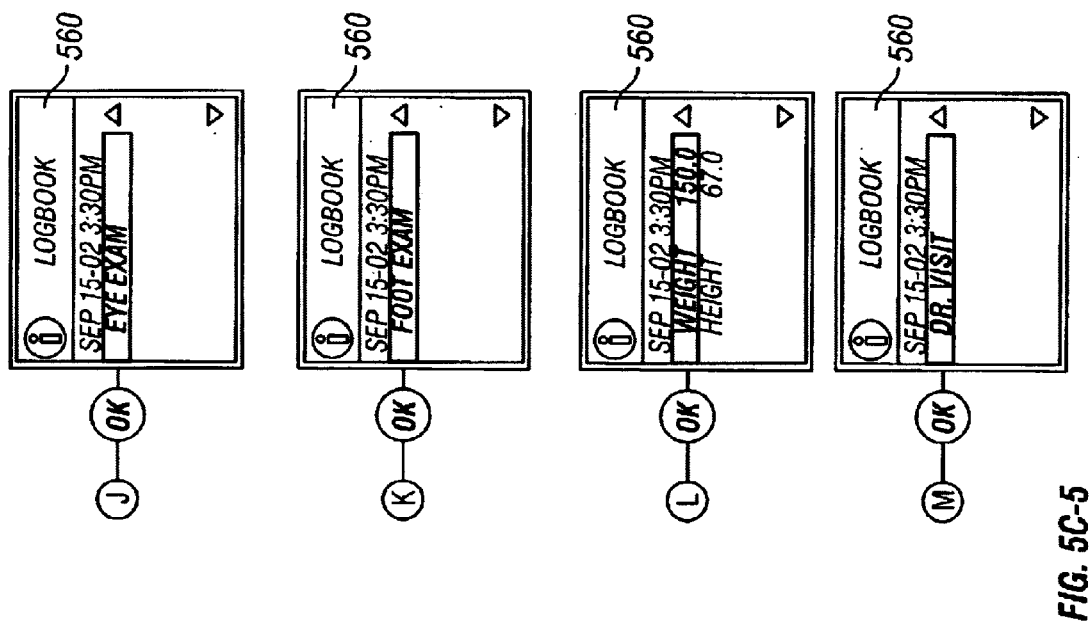

Referring to FIG. 5c, the generalised lifestyle data entry sequence (400) is now described in detail specifically in relation to entry of lifestyle data in the health category. Upon operation of the health function-specific button (112), the time options (402), as described above, are displayed in the user interface (250). Having selected the time and date information, health sub-category options (534), specifically labelled "Health Notes" and "Health Checks" are displayed in the user interface (250) for selection.

Selection of the "Health Notes" health sub-category option (534a), displays in the user interface (250) additional selectable health values (538) labelled "Stress", "Feel Hypo", "Illness", "Menses", "Vacation" and "Other". Selection of one of the selectable health values (538) immediately transfers a corresponding comment with the time and date information into the memory (202). Following entry of lifestyle data for the "Health Notes" health sub-category option (534a), the logbook (560) (see below) is displayed in the user interface (250).

Selection of the "Health Checks" health sub-category option (534b), displays in the user interface (250) selectable health value options (536) labelled "Ketones", "HbA1c", "Microalbumin", "Cholesterol", "Blood pressure", "Eye Exam", "Foot Exam", "Weight/Height" and "Dr. Visit".

Selection of one of the selectable health value options (536) labelled "Ketones", "HbA1c", "Microalbumin", "Cholesterol", "Blood pressure" or "Weight/Height" displays one or more selectable health values (538), thereby permitting entry of one or more appropriate numerical values, which might be measured analyte levels, blood pressure, weight or height. Other possible analyte levels could also be measured, such as High Density Lipoprotein (HDL), Low Density Lipoprotein (LDL) or triglyceride levels, for which there would be appropriate selectable health value options (536). Any entered health values (538) are stored in the memory (202) with the time and date information and a pointer to a corresponding health value option.

Previously selected health values (538) are used as default health values, in that a previously entered health value for a given selectable health value option becomes the health value (538) which is initially highlighted upon selection of a given selectable health value option (536). Thus, the user interface (250) provides for intelligent interaction between a user and the testing device (100). Additionally, use of the cursor key (122) is minimised. Accordingly, the general usability of the testing device (100) is improved.

Selection of one of the selectable health value options (536) labelled "Eye Exam", "Foot Exam" or "Dr. Visit" causes a confirmation message (539) to be displayed in the user interface (250), requesting confirmation that a marker for one of these aforementioned selectable health value options (536) should be input into the memory (202). Further operation of the OK button (118) immediately stores in the memory (202) a marker for the selected health value option with the time and date information.

Following entry of lifestyle data for the health category labelled "Health Checks", the aforementioned health value options (536) for the "Health Checks" health sub-category (534b) are again displayed in the user interface (250). This way, further health-checkup related information can be immediately entered, if required.

Figure 5D:
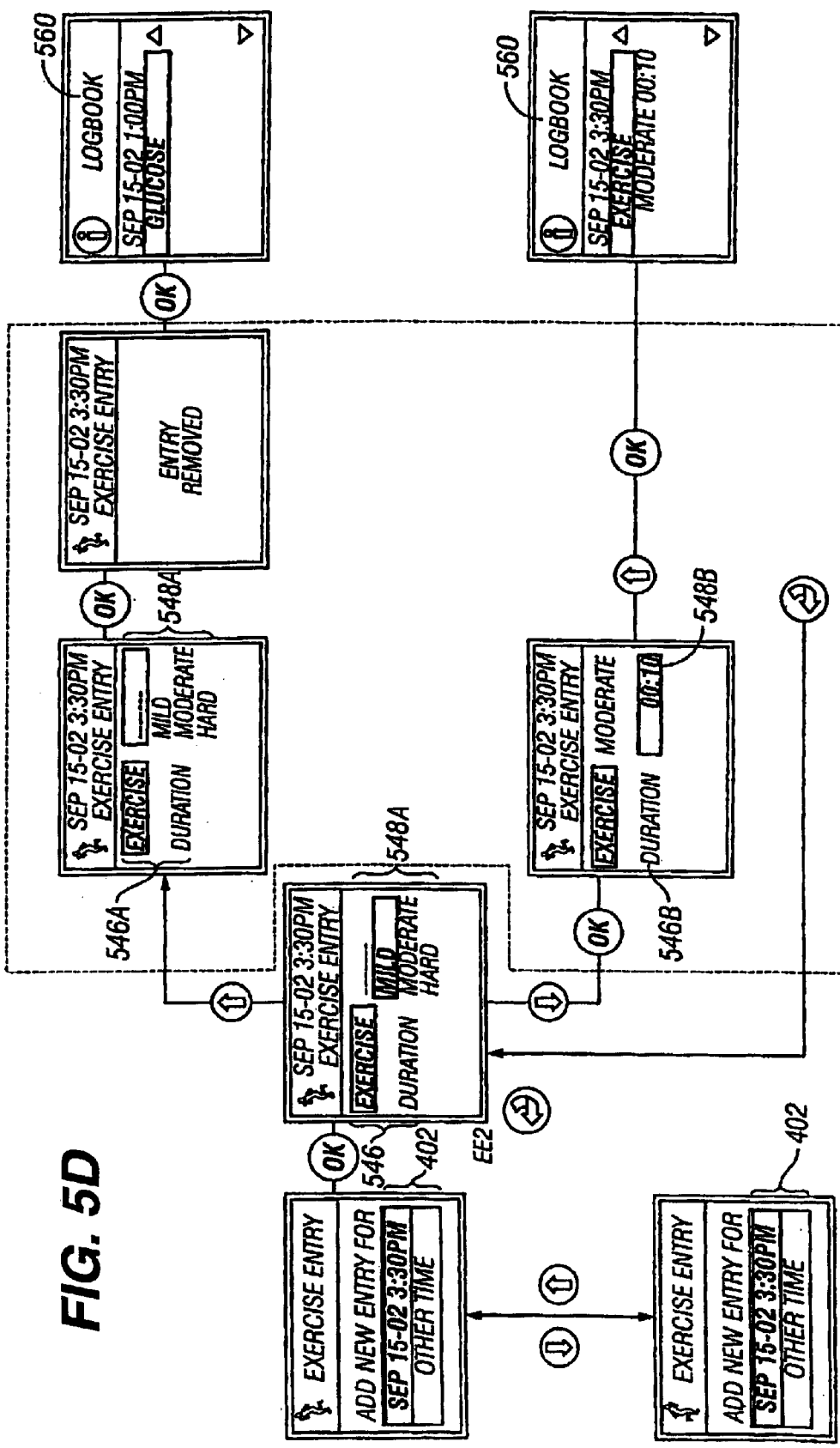

Referring to FIG. 5d, the generalised lifestyle data entry sequence (400) is now described in more detail specifically in relation to entry of lifestyle data in the exercise category. Upon operation of the exercise function-specific button (114), the time options (402), as described above, are displayed in the user interface (250). Having selected the time and date, selectable exercise value options (546), specifically labelled "Exercise" and "Duration" are displayed in the user interface (250) for selection (there are no exercise sub-category options for entry of lifestyle data in the exercise category).

For the "Exercise" selectable exercise value option (546a), selectable exercise type values (548a) corresponding to an intensity of exercise can be selected, specifically "Mild", "Moderate" and "Hard". Additionally there is a selectable exercise value labelled as "-----", selection of which skips the entry of data and displays a logbook (560) in the user interface (250) (see below). Following selection of one of the selectable exercise duration values (548a), the "Duration" selectable exercise value option (546b) is highlighted and selectable exercise duration values (548b) corresponding to a duration of exercise can be entered. Similarly, there is a numerical value labelled "------", selection of which skips the entry of data and displays a logbook (560) in the user interface (250) (see below). Following selection of one of the selectable exercise duration values (548b) by operation of the OK button (118), the values for the exercise intensity and duration are transferred to the memory (202).

Following entry of lifestyle data for the exercise category, the logbook (560) (see below) is displayed in the user interface (250).

Figure 6A:
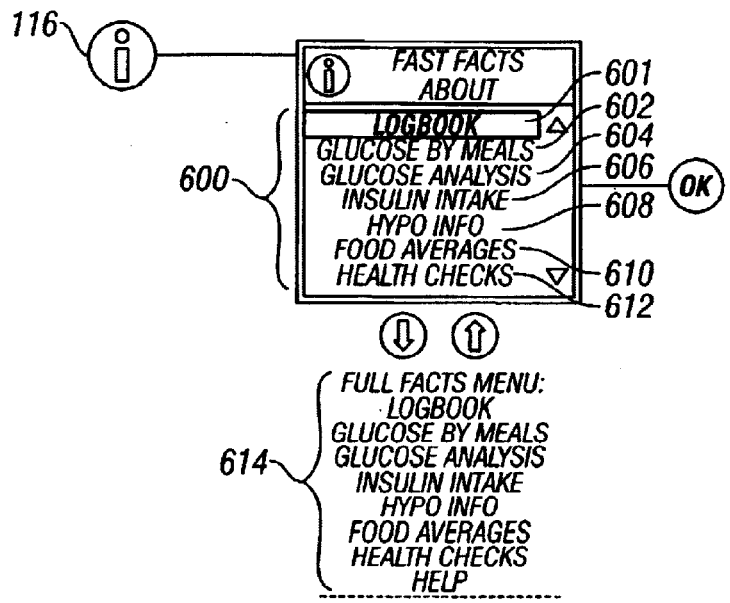
FIG. 6a shows an information menu displayed in a user interface of the testing device of FIG. 1 for displaying data stored in the testing device.

Referring to FIG. 6a, the user interface (250) displays menu options (600) upon operation of the information button (116). The information button (116) is referred to as a "FastFacts" button and the menu options (600) are collectively referred to as a "FastFacts Menu".

In the embodiment shown in FIG. 6a, the menu options (600) are entitled: "Logbook", "Glucose by Meals", "Glucose Analysis", "Insulin Intake", "Hypo Info", "Food Averages", "Health Checks" and "Help".

Selection of the "Logbook" menu option (601) causes a logbook (see below) to be displayed in the user interface (250).

Selection of the "Glucose by Meals" menu option (602) allows measured glucose levels to be displayed for each day prior to the current day. The analysis means (254) averages measured glucose levels stored in the memory (202) and displays on the display screen (106) for each day in one of the following four time-period categories: (a) before and after breakfast; (b) before and after lunch; (c) before and after dinner; and (d) night. The time-periods for the aforementioned categories are pre-defined through a set-up sequence of the testing device (see below).

Selection of the "Glucose Analysis" menu option (604) causes further menu options to be displayed relating to the analysis of measured glucose levels. Measured glucose levels stored in the memory (202) can be displayed graphically (i.e. points plotted on a graph of date against measured glucose level) or in tabular form. The analysis means (254) receives measured glucose levels from the memory (202) and passes analytical results to the user interface generation means (252) for displaying or plotting graphically on the display screen (106). Measured glucose levels for each day can be displayed or the time of day can be selected (i.e. before breakfast, after breakfast, before lunch, after lunch, before dinner, after dinner or night) such that only measured glucose levels for these particular time periods of day are plotted on the display screen (106). In addition, values for averages of all glucose levels stored in the memory (202) can be calculated over a number of different time periods (e.g. 7, 14, 30, 60 and 90 days) and all displayed together on the display screen (106).

A user can easily navigate back for re-selection of the time period by operation of the back button (120). A longer or shorter time period can then be highlighted by operation of the cursor button (122) and selected by operation of the OK button (118) to view different results. Repetition of this procedure can help identify treatment trends or the impact of changes in treatment or lifestyle and its impact on measured glucose levels over time.

In a similar manner, values for averages of all glucose levels stored in the memory (202) can be calculated for each time period of a day (as mentioned above) and displayed on the display screen (106). Moreover, values for averages of all glucose levels stored in the memory (202) can be calculated over a number of different time periods and displayed for three exercise periods, specifically "before exercise", "during exercise" and "after exercise". Another analysis method allows range information to be displayed on the display screen. Such range information shows the proportions of averaged measured glucose levels which are above, within or below pre-defined ranges. Such ranges are determined in a testing device set-up sequence (see below). The range information is viewed as a percentage either before or after one of four pre-defined meal time-period categories (i.e. breakfast, lunch, dinner or night).

Selection of the "Insulin Intake" menu option (606) causes further menu options to be displayed relating to the intake of insulin, data for which has been entered through prior operation of the medication function-specific button (110). In particular, the intake of different amounts of different types of insulin specified in a set-up sequence of the testing device (see below) can be viewed as average amounts over a given time period or as total amounts on each day prior to the current day. Analysis means (254) processes the stored insulin data. In addition, the total and average intake of insulin can be viewed on the display screen (106). Specifying the type of insulin may include specifying whether the insulin is given through a syringe or pump, or taken as a pill or inhaled.

Selection of the "Hypo Info" menu option (608) allows incidents of the diabetic "hypo" condition to be viewed. The "hypo" condition is pre-defined in the testing device set-up sequence (as described below) as a configurable glucose level below which a diabetic individual is considered as being "hypo". The incidents of the diabetic "hypo" condition are viewed as the number of incidents which have occurred in a chosen time period for each of the following times of day: before breakfast, after breakfast, before lunch, after lunch, before dinner, after dinner and night.

Selection of the "Food Averages" menu option (610), allows averages for previously entered data stored in the memory (202) relating to food consumption of an individual to be displayed on the display screen (106). The analysis means (254) processes stored food related data according to options selected in the user interface (250) through operation of the navigation buttons (104). Carbohydrate and fat levels, calorific content and protein intake for each predefined time-period: "Breakfast", "Lunch", "Dinner" and "Snack" can be averaged by the analysis means (254) over selected time-periods and displayed on the display screen (106).

Selection of the "Health Checks" menu option (612) allows averages for entered data stored in the memory (202) relating to health checkups of an individual to be displayed on the display screen (106). Displayed in the user interface (250) are the selectable health value options (536) relating to health checkups of an individual, along with the date of the last checkup and a value measured at the last checkup.

Selection of the "Help" menu option (614) (not shown in FIG. 6a), causes contact information for help in using the testing device (100) to be displayed on the display screen (106). For example such contact information may read "Contact LifeScan Customer Service or visit the Website at www.LifeScan.com".

Figure 6B:
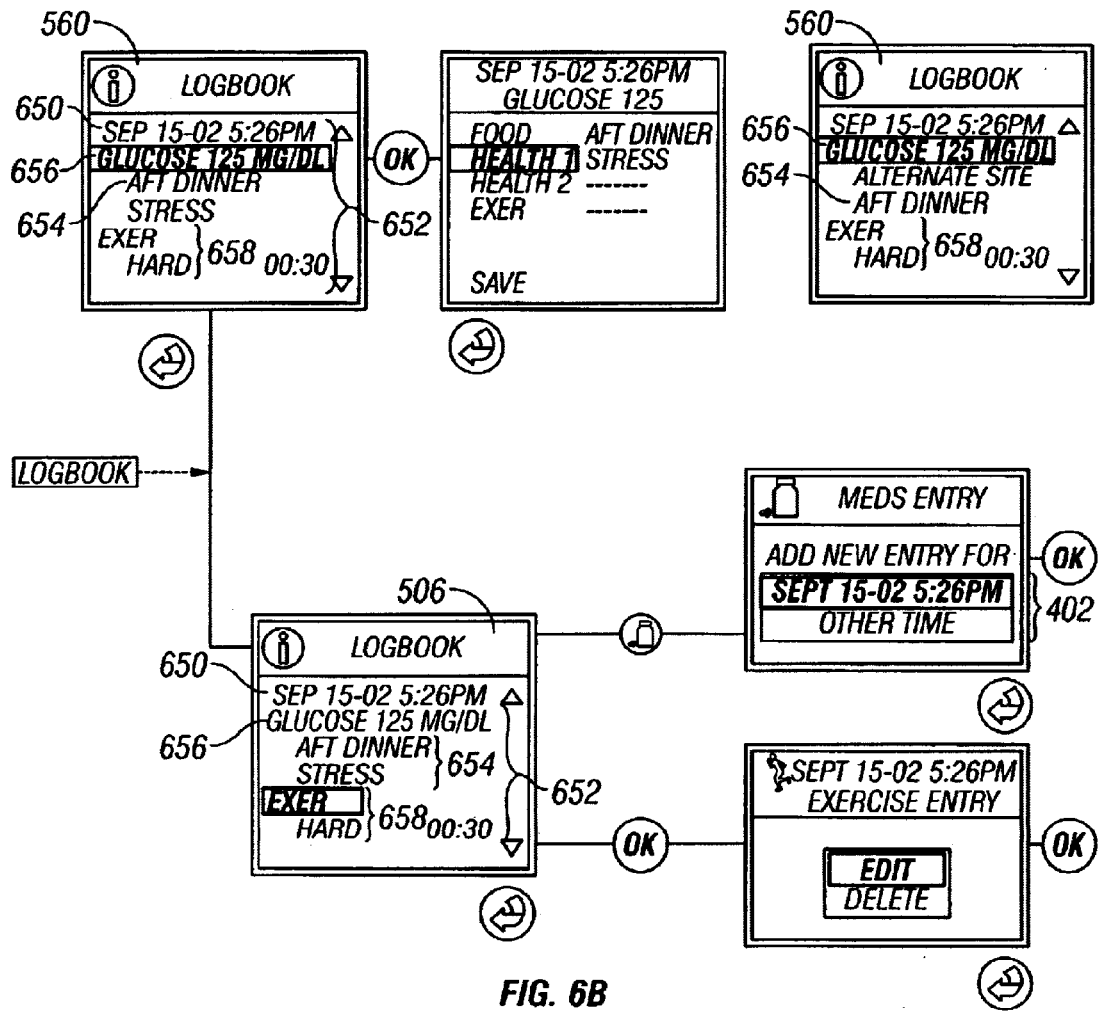
FIG. 6b shows a sample logbook screen displayed in the user interface of the testing device of FIG. 1 for displaying data stored in the testing device.

Referring to FIG. 6b, a logbook (560) is displayed in the user interface (250) following selection of the "Logbook" menu option (601). Date and time records (650) stored in the memory (202) are displayed in the user interface (250) with associated data records (652), such as stored glucose levels and/or lifestyle data. Glucose levels are displayed with associated glucose comments (654) (see below). Operation of the navigation buttons (104) allows each data record (652) to be scrolled though in date and time order, with each record for a particular date and time being highlighted in turn, before the next time and date and corresponding records are displayed in the user interface (250). Each data record (652) can be highlighted in turn by the navigation buttons (104) and selected by operation of the OK button (118). Selection of a glucose data record (656) allows a glucose comment (see below) to be entered for the selected glucose data record. Selection of a lifestyle data record (658) displays two options, labelled "Edit" and "Delete", selection of which allows the selected lifestyle data record to be edited or deleted easily with few operations of the navigation buttons (104). The sequence for editing of lifestyle data is similar to the generalised lifestyle data entry sequence (400) described above, except that previously entered values for the lifestyle data record being edited are pre-selected by the user from the logbook (560).

Operation of one of the function-specific buttons (102) corresponding to a particular category of lifestyle data, whilst viewing the logbook (560), allows immediate entry of lifestyle data using the time and date currently being shown in the user interface (250).

Figure 7A:
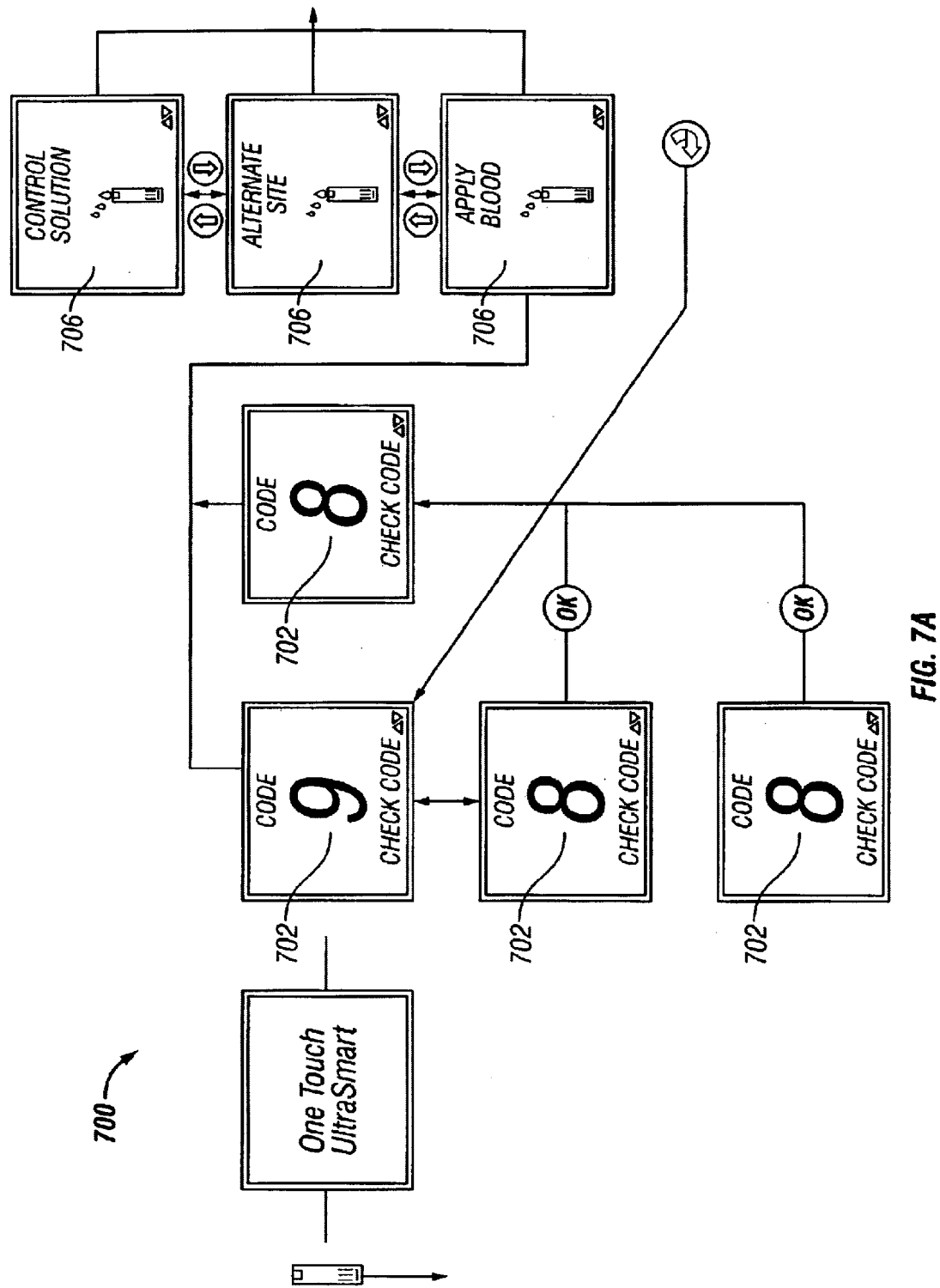
FIG. 7 shows a testing sequence for measuring glucose levels with the testing device of FIG. 1 through use of a test-strip inserted into the testing device.
Figure 7B:
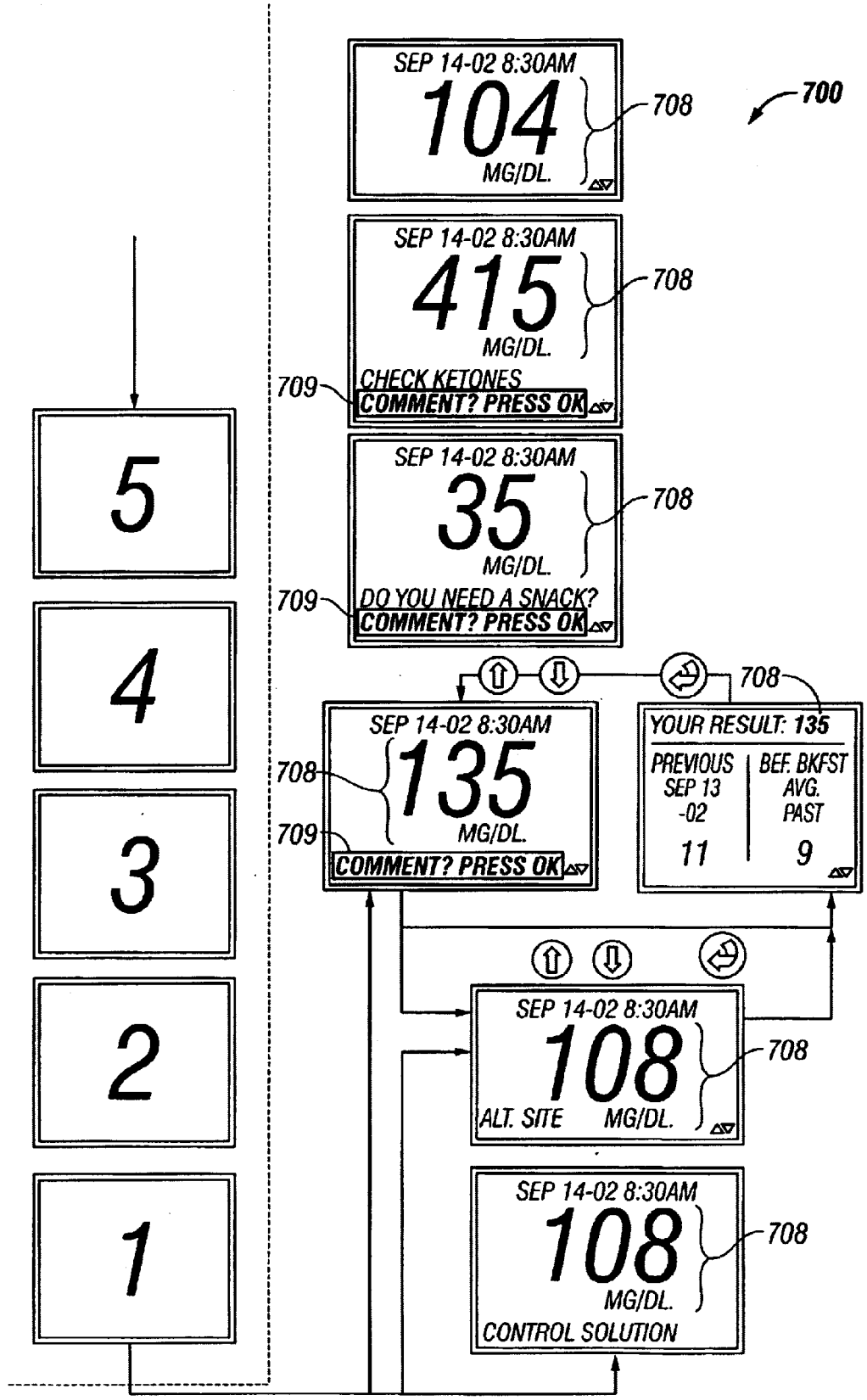

Referring to FIG. 7, a testing sequence (700) for measuring a glucose level (708) of an individual is shown. A test-strip is inserted into the test-strip port (124), which immediately turns on the testing device (100). A default code (702) relating to calibration parameters used with the testing device for a particular type of test-strip is displayed in the display screen (106). The code (702) can be changed by operation of the cursor button (122) and selected by operation of the OK button (118). If a particular type of test-strip has previously been used with the testing device (100) on a pre-defined number of occasions, then the corresponding code (702) of the test-strip is stored in the memory (202) and used as a default code (702), which is initially displayed in the display screen (106) of the testing device (100) following insertion of a test-strip into the test-strip port (124). Unless the code (702) is changed, as described above, then after a pre-defined time period, then default code (702) is automatically selected without a user having to operate the OK key (102). However, following selection of the code (702), operation of the back button (120) allows a user to reselect the code (702).

Following selection of the code (702), one of a plurality of messages (706) is displayed on the display screen (106), requesting a blood sample to be applied to the test-strip. At this stage, operation of the cursor button (122) cycles through three messages (706) on the display screen (106), specifically "Apply Blood", "Alternate Site" and "Control Solution". This way, the testing device (100) can recognise for each individual measured glucose level (708) that a control solution is being applied to the test-strip or that blood is being taken from an alternate site on an individual. Normally, blood samples would be taken from the same bodily location on an individual. However, sometimes another location, an "alternate site", might be used, for example if the one bodily location becomes sensitive or inconvenient. For example, an alternate site might refer to an upper arm location if a lower arm location is normally used. If an alternate site for sampling of blood is used, it is important that this is recognised, particularly when analysis of the measured glucose levels is being performed at a later stage. Such information could be used in any future general investigation, using a number of people, into any differences in analyte levels in blood samples extracted from different locations on the body.

When an appropriate message is displayed on the display screen (106), a solution, blood or otherwise, can be applied to the test-strip. Measurement of a glucose level in the solution takes place following application of the solution to the test-strip. The measured glucose level (708) is displayed in the display screen (106) and stored in the memory (202) together with the date and time of day and whether the blood sample was taken from an alternate site on an individual. If the measured glucose level (708) lies outside a pre-defined target range, then the prompt means (256) instructs the user interface generation means (252) to display a message (709) in the user interface (250) prompting a user of the testing device (100) to press the OK button (118), so that lifestyle data in the form of glucose comments (see below) which are associated with the measured glucose level (708) can be entered. Two pre-defined target ranges can be specified for each meal time, specifically for a period before and after each meal time. Thus, by pressing one of the navigation buttons (104), in this case the OK button (118), lifestyle data can be entered immediately. This way, when the measured glucose level (708) is outside a pre-defined target range (as specified in the testing device set-up sequence (see below)) a user is automatically prompted to enter a glucose comment. Thus, improved diagnosis on out-of-range glucose levels can made by a physician at a later stage.

If the measured glucose level (708) additionally lies below a pre-defined glucose "Hypo" level, then a further message is displayed on the display screen (106) querying whether a user of the testing device (100) should consider having a snack.

Figure 8:
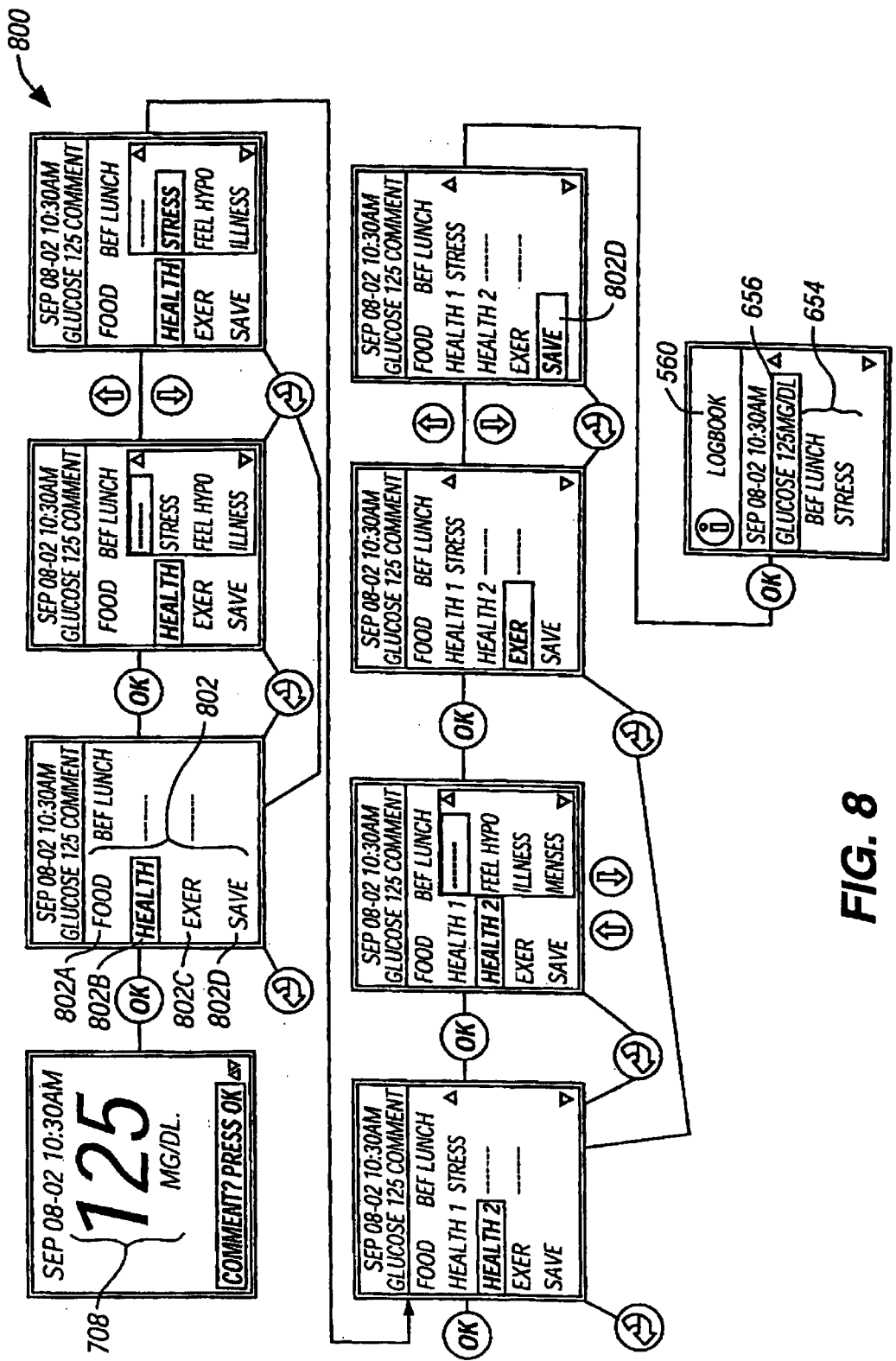
FIG. 8 shows a generalised sequence for entering health, exercise and food comments following measurement of a glucose level.

Referring to FIG. 8, operation of the OK button (118), following measurement of a glucose level, immediately starts a glucose comment insertion sequence (800). Glucose comments (654) are descriptive comments which fall into one of a number of glucose comment sub-categories (802), specifically a food comment sub-category, a health comment sub-category and an exercise comment sub-category. The glucose comments (654) are stored in the memory with an associated measured glucose level (708) and are displayed in the logbook (560). Thus, the status of an individual's food intake, health or exercise level can be immediately entered at the time of measurement of a glucose level. Additionally, the glucose comment insertion sequence (800) can be initiated from the logbook (560) by operation of the OK button (118) when a glucose data record (656) is highlighted in the user interface (250).

Each of the glucose comment sub-categories (802) can be highlighted in turn by operation of the cursor button (122) and selected by operation of the OK button (118). For each of the glucose comment sub-categories (802), there are a number of different glucose comments (654) which can be highlighted by operation of the cursor button (122) and selected by operation of the OK button (118). For each of the glucose comment sub-categories (802), one of the glucose comments (654) can be selected, except for the health comment sub-category (802b), for which, following insertion of one health glucose comment, causes the user interface (250) to be adapted such that an additional health glucose comment can be inserted. This way, up to six health glucose comments can be selected and stored with the measured glucose level (708) in the memory (202).

For the food glucose comment sub-category (802a), the following food glucose comments (654a) can be selected and stored in the memory (202): "Bef Brkft", "Aft Brkft", "Bef Lunch", "Aft Lunch", "Bef Dinner", "Aft Dinner" and "Night", corresponding to before breakfast, after breakfast, before lunch, after lunch, before dinner, after dinner and night. For the health glucose comment sub-category (802b), the following health glucose comments (654b) can be selected and stored in the memory (202): "Stress", "Feel Hypo", "Illness", "Menses", "Vacation" and "Other", having self-explanatory meanings. For the exercise glucose comment sub-category (802c), the following exercise glucose comments (654c) can be selected and stored in the memory (202): "Before", "During" and "After", having self-explanatory meanings.

Also displayed in the user interface (250) with the glucose comment sub-categories is a "Save" option (802d), which can be highlighted by operation of the cursor button (122). Selection of the "Save" option (802d) causes the transfer means (258) to transfer the measured glucose level (708), with any glucose comments (654) which have been entered, into the memory (202) with time and date information.

The testing device (100) has a set-up sequence which is initiated when the testing device (100) is used for the first time or when the OK button (118) and the back button (120) are operated together. The set-up sequence allows customisation of the operation of the testing device (100) through the user interface (250). Customisable settings are stored in the memory (202) for use in data entry, display or analysis. In particular, the following are examples of customisable settings: the language used in the user interface (250), the current time and date, the number of doses and types of insulin taken by an individual using the testing device (100), whether an insulin pump is used by a user using the testing device (100) and the number and type of different pills taken by an individual using the testing device. Additionally, the times of day for different meal periods (i.e. before breakfast, after breakfast, before lunch, after lunch, before dinner, after dinner and night) can be set. Glucose level ranges which are displayed as horizontal lines on any graphs displayed by the testing device (100) in the display screen (106) can be specified for "before" and "after" meal periods. Furthermore, a "Hypo" level can be set, which specifies a glucose level used to compare against measured glucose levels and generate a warning if a measured glucose level (708) is below this "Hypo" level.

The prompt means (256) can also immediately generate non-customisable warnings on the display screen (106) for high measured glucose levels (above 600 mg/dL) and low measured glucose levels (below 20 mg/dL).

In conclusion, the testing device of the present invention significantly reduces the obstacles associated with maintaining an accurate record of an individual's lifestyle. The present invention promotes frequent monitoring for diabetic individuals by providing a simple, efficient way of recording, not only blood glucose levels, but also other information which is likely to affect an individual's prognosis. By logging glucose and lifestyle information in the manner described herein, the testing device provides and effective medication recordal system. For instance, in the United States the device meets the requirements of the National Committee for Quality Assurance's (NCQA) Health Plan Employer Data and Information Set (HEDIS®). HEDIS® provides standardised performance measures for providing individuals with information needed to reliably compare the performance of managed health care plans.

It will of course be understood that the present invention has been described purely by way of example only and that modifications of detail can be made within the scope of the invention.

What is claimed is:

1. A testing device for testing an analyte in a sample of bodily fluid, comprising:
   memory storing data, said data being analyte data related to analyte measurements carried out by the testing device and lifestyle data, and the analyte data includes a pointer to a bodily location from which an analyte sample was taken by an individual using the testing device, wherein the testing device utilizes a plurality of data pointers, each of said data pointers indicating a separate bodily location;
   initiation means for initiating immediate entry of data related to a specific category of lifestyle data,
   navigation means for entry and navigation of said data; and
   transfer means for transferring said data to said memory.

2. A testing device according to claim 1, further comprising a display screen, wherein the transfer means is a processor, the processor being adapted to access the data stored in the memory and display said data on the display screen.

3. A testing device according to claim 2, wherein the processor is further adapted to perform an analysis on the data and display results of said analysis on the display screen.

4. A testing device according to claim 3, wherein said analysis includes determining whether data lies outside a predetermined range, such that if said data lies outside that predetermined range, the analysis means displays a prompt on the display screen requesting input of one or more comments from a user of the testing device.

5. A testing device according to claim 3, wherein said analysis comprises averaging data stored in the memory over a predetermined time period.

6. A testing device according to claim 3, wherein said navigation means is adapted to select data for analysis or for display on the display screen.

7. A testing device according to claim 1, wherein said lifestyle data is stored in the memory as lifestyle records, each lifestyle record comprising:
   a date and time-stamp;
   a pointer to a lifestyle event; and
   a lifestyle value.

8. A testing device according to claim 1, wherein said analyte data is stored in the memory as analyte records, each analyte record comprising:
   a data and time-stamp; and
   an analyte value.

9. A testing device according to claim 1, wherein each analyte record further comprises:
   a pointer to a bodily location from which an analyte sample was taken by an individual using the testing device;
   a pointer to a lifestyle event; and
   a lifestyle value.

10. A testing device according to claim 1, wherein said initiation means is a plurality of function-specific buttons, each function-specific button corresponding to a specific category of lifestyle data.

11. A testing device according to claim 1, further comprising communication means adapted to transfer data between said memory and an external device.

12. A testing device according to claim 1, wherein the testing device is a glucose meter and one of the analytes being tested is glucose.

13. A testing device for testing an analyte in a sample of bodily fluid, comprising:
    memory for storing analyte data; and
    navigation means,
    wherein:
    said sample of bodily fluid is usually obtained from a specific bodily location on an individual; and
    said navigation means is adapted to flag analyte data stored in the memory if said sample of bodily fluid is obtained from an alternate bodily location other than said specific bodily location following a carrying out of an analyte measurement.

14. A testing device according to claim 13, wherein said navigation means is further adapted to indicate to the memory said alternate bodily location, such that a pointer to said alternate location is stored with associated analyte data in the memory.

15. A testing device according to claim 14, further comprising a display screen, wherein said navigation means comprises a cursor button and an OK button, such that operation of the cursor button adapts the display screen to display one or more alternate bodily location options corresponding to one or more alternate bodily locations and operation of the OK button send said alternate bodily location to the memory.

16. A method of storing analyte data in a testing device for testing an analyte in a sample of bodily fluid, said method comprising the steps of:
    obtaining a sample of bodily fluid from a bodily location, said sample of bodily fluid normally being obtained from a specific bodily location on an individual;
    measuring an analyte level in the sample of bodily fluid;
    storing said analyte level in memory in the testing device; and
    flagging said analyte level in the memory if said sample of bodily fluid was obtained from an alternate bodily location other than said specific bodily location.

17. A method according to claim 16, wherein the step of flagging said analyte level in the memory comprises storing a pointer to said alternate bodily location with said analyte leveling the memory.

* * * * *